United States Patent
Chaisson et al.

(10) Patent No.: US 8,911,972 B2
(45) Date of Patent: Dec. 16, 2014

(54) SEQUENCING METHODS USING ENZYME CONFORMATION

(75) Inventors: Mark Chaisson, San Francisco, CA (US); Sonya Clark, Oakland, CA (US); Christopher Silk, Oakland, CA (US); John Lyle, Redwood Shores, CA (US); Lei Jia, Palo Alto, CA (US); Keith Bjornson, Union City, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 637 days.

(21) Appl. No.: 12/967,507

(22) Filed: Dec. 14, 2010

(65) Prior Publication Data

US 2011/0160077 A1 Jun. 30, 2011

Related U.S. Application Data

(60) Provisional application No. 61/287,053, filed on Dec. 16, 2009.

(51) Int. Cl.
*C12P 19/34* (2006.01)
*C12Q 1/68* (2006.01)

(52) U.S. Cl.
CPC .................................. *C12Q 1/6869* (2013.01)
USPC ...................................................... 435/91.2

(58) Field of Classification Search
None
See application file for complete search history.

(56) References Cited

U.S. PATENT DOCUMENTS

| | | | |
|---|---|---|---|
| 5,328,824 A | 7/1994 | Ward et al. | |
| 5,476,928 A | 12/1995 | Ward et al. | |
| 6,699,723 B1 | 3/2004 | Weiss et al. | |
| 6,861,155 B2 | 3/2005 | Bawendi et al. | |
| 6,908,736 B1 * | 6/2005 | Densham | 435/6.1 |
| 7,041,812 B2 | 5/2006 | Kumar et al. | |
| 7,235,361 B2 | 6/2007 | Bawendi et al. | |
| 2002/0127623 A1 | 9/2002 | Minshull et al. | |
| 2003/0124576 A1 | 7/2003 | Kumar et al. | |
| 2007/0072196 A1 | 3/2007 | Xu et al. | |
| 2007/0196846 A1 | 8/2007 | Hanzel et al. | |
| 2008/0108082 A1 | 5/2008 | Rank et al. | |
| 2010/0075332 A1 | 3/2010 | Patel et al. | |
| 2010/0093555 A1 | 4/2010 | Bjornson et al. | |
| 2010/0112645 A1 | 5/2010 | Clark et al. | |

FOREIGN PATENT DOCUMENTS

| | | |
|---|---|---|
| EP | 1368460 B1 | 10/2007 |
| WO | 9013666 A1 | 11/1990 |
| WO | 9833939 A1 | 8/1998 |
| WO | 0125480 A2 | 4/2001 |

(Continued)

OTHER PUBLICATIONS

Allen, W. J., P. J. Rothwell, et. al. (2008), "An intramolecular FRET system monitors fingers subdomain opening in Klentaq1." Protein Sci 17(3): 401-8.

(Continued)

*Primary Examiner* — Suchira Pande
(74) *Attorney, Agent, or Firm* — Robert H. Reamey

(57) ABSTRACT

Systems and methods are provided for single-molecule sequencing of template nucleic acids in which the signal from a label attached to a polymerase enzyme is used to monitor conformational changes in the polymerase which occur while labeled nucleotides or nucleotide analogs are added to a growing nucleic acid chain which is complementary to the template nucleic acid. The signal indicative of the conformational state of the enzyme is used to determine with higher confidence when true nucleotide or nucleotide analog incorporation events occur, allowing for the improved quality of base calls and sequence determination.

18 Claims, 11 Drawing Sheets

(56) References Cited

FOREIGN PATENT DOCUMENTS

| | | |
|---|---|---|
| WO | 2007075987 A2 | 7/2007 |
| WO | 2007076057 A2 | 7/2007 |
| WO | 2008051530 A2 | 5/2008 |

OTHER PUBLICATIONS

Beese, et al., "Structural Basis for 3'-5' Exonuclease Activity of *Escherichia coli* DNA Polymerase I: A Two Metal Ion Mechanism," EMBO J (1991) 10(1)25-33.

Berman et al. (2007) "Structures of phi29 DNA polymerase complexed with substrate: The mechanism of translocation in B-family polymerases" EMBO J. 26:3494-3505.

Blanco, L. and M. Salas (1996), "Relating structure to function in phi29 DNA polymerase." J Biol Chem 271(15):8509-12.

Boon et al. "An electrical probe of protein-DNA interactions on DNA-modified surfaces" Nat. Biotechnol. 20(3), 282-286, 2002.

Christian, T.D. et al. PNAS, 106(50), 21109-21114.

Popp et al. Curr Protoc Protein Sci. Apr. 2009;Chapter 15:Unit 15.3.

Doublie, S., M R. Sawaya, et al. (1999). "An open and closed case for all polymerases," Structure 7(2): R31-5.

Eid et al, Science, 323, 133-138, 2009.

Furey et al., Biochemistry, 37:2979-2990, 1998.

Ha et al., "Single Molecule Fluorescence Spectroscopy of Enzyme Conformational Dynamics and Cleavage Mechanism." Proc. Natl. Acad. Sci. USA, 1999; 96:893.

Dif et al., J Am Chem Soc. Oct. 21, 2009; 1(41):14738-46.

Joyce et al. "Techniques used to study the DNA polymerase reaction pathway" Biochim Biophys Acta. doi:10.1016/j, bbapap.2009.07.021.

Joyce, C. M. and T. A. Steitz (1994). "Function and structure relationships in DNA polymerases." Annu Rev Biochem 63: 777-822.

Kamtekar et al. (2004) "Insights into strand displacement and processivity from the crystal structure of the protein-primed DNA polymerase of bacteriophage Φ29" Mol. Cell 16(4): 609-618).

Kamtekar et al. (2006) "The phi29 DNA polymerase:protein-primer structure suggests a model for the initiation to elongation transition" EMBO J. 25(6):1335-43.

Kiick, Kristi L. et al., "Incorporation of azides into recombinant proteins for chemoselective modification by the Staudinger ligation." PNAS 2002 99:19-24; published online before print Dec. 18. 2001, doi;10.1073/pnas.012583299.

Korlach et al., Nucleosides, Nucleotides and Nucleic Acids, 27:1072:1083. 2008.

Luo et al. PNAS, 104(31) 12610-12615, 2007.

Oliis, D. L., P. Brick, et al. (1985). "Structure of large fragment of *Escherichia coli* DNA polymerase I complexed with dTMP." Nature 313(6005): 762-6.

Santoso, et al, "Conformational Transitions in DNA Polymerase I Revealed by Single-Molecule FRET." PNAS (2010) 107(2):715-720.

Schutz et al., Biophys. J., 1998; 74:2223-6.

Machleidt et al., Series: Methods in Molecular Biology | Volume: 356 | Pub. Date: Aug. 15, 2006 | Page Range: 209-220.

Ignatova et al., Series: Methods in Molecular Biology | vol. 490 | Pub. Date: Mar. 1, 2008 | Page Range: 1-14.

Steitz, T. A. (2006). "Visualizing polynucleotide polymerase machines at work." EMBO J 25(15): 3458-68.

Steitz, T. A. and Y. W. Yin (2004). "Accuracy, lesion bypass, strand displacement and translocation by DNA polymerases." Philos Trans R Soc Lond B Biol Sci 359(1441): 17-23.

Steitz, T.A., et al., "DNA Polymerases: Structural Diversity and Common Mechanisms." Journ Biol Chem (1999) 274 (25): 17395-98.

Wang, Q. et al., "Bioconjugation by Copper(I)-Catalyzed Azide-Alkyne [3+2] Cycloaddition." J. Am. Chem. Soc., 2003, 125 (11), pp. 3192-3193.

\* cited by examiner

SEQUENCING METHODS USING ENZYME CONFORMATION

CROSS-REFERENCE TO RELATED APPLICATIONS

This application claims the benefit of U.S. Provisional Patent Application No. 61/287,053 filed Dec. 16, 2009, the disclosure of which is incorporated herein by reference in its entirety for all purposes.

STATEMENT REGARDING FEDERALLY SPONSORED RESEARCH

Not Applicable.

BACKGROUND OF THE INVENTION

Nucleic acid sequences encode the necessary information for living things to function and reproduce, and are essentially a blueprint for life. Determining such sequences is therefore a tool useful in pure research into how and where organisms live, as well as in applied sciences such drug development. In medicine, sequencing tools can be used for diagnosis and to develop treatments for a variety of pathologies, including cancer, heart disease, autoimmune disorders, multiple sclerosis, or obesity. In industry, sequencing can be used to design improved enzymatic processes or synthetic organisms. In biology, such tools can be used to study the health of ecosystems, for example, and thus have a broad range of utility.

An individual's unique DNA sequence provides valuable information concerning their susceptibility to certain diseases. The sequence will provide patients with the opportunity to screen for early detection and to receive preventative treatment. Furthermore, given a patient's individual blueprint, clinicians will be capable of administering personalized therapy to maximize drug efficacy and to minimize the risk of an adverse drug response. Similarly, determining the blueprint of pathogenic organisms can lead to new treatments for infectious diseases and more robust pathogen surveillance. Whole genome DNA sequencing will provide the foundation for modern medicine. Sequencing of a diploid human genome requires determining the sequential order of approximately 6 billion nucleotides. Sequencing of RNA can also provide valuable information relating to which portions of the genome are being expressed by single cells or groups of cells. Greater knowledge of expression can provide keys to understanding and treating many diseases and conditions, including providing a molecular level understanding of the progression of cancer.

A variety of methods have been developed with the goal of providing efficient, cost effective, accurate, and high throughput sequencing. Single-molecule nucleic acid sequencing-by-synthesis is a sequencing method that has the potential to revolutionize the understanding of biological structure and function. While such sequencing methods have been shown to provide reliable sequencing information, further improvements in the quality of sequencing information is desired. For example, in current sequencing-by-synthesis methods, errors in sequencing can occur due to events such as branching and sticking. The present invention provides systems and methods of for improving the quality of nucleic acid sequence information.

BRIEF SUMMARY OF THE INVENTION

In one aspect, the invention provides a method of sequencing comprising; providing a single polymerase enzyme complex comprising a polymerase enzyme, a nucleic acid template, and a primer; wherein the polymerase enzyme comprises a label which has a signal that changes when the enzyme undergoes a conformational change; contacting the complex with sequencing reagents including two or more types of nucleotides or nucleotide analogs, each labeled with a different label, whereby enzyme mediated addition of nucleotides or nucleotide analogs to the primer to produce a growing strand complementary to the template occurs; observing signals from the labeled nucleotides or nucleotide analogs and signals from the labeled enzyme during the enzyme mediated addition; and determining the type of the nucleotides or nucleotide analog that is added to the growing strand using the observed signal from the label of that nucleotide or nucleotide analog; whereby observed signals from the labeled polymerase enzyme are used to indicate whether a type of nucleotide or nucleotide analog is incorporated into the growing strand.

In some embodiments the labels for the enzyme and the nucleotides or nucleotide analogs comprise fluorescent labels. In some embodiments the signal that changes when the enzyme undergoes a conformational change comprises a FRET signal from a donor and an acceptor. In one embodiment. In some embodiments the donor and acceptor are both attached to the polymerase enzyme. In some embodiments the donor and acceptor are attached to portions of the enzyme which move relative to one another during a conformational change.

In some embodiments the label whose signal changes when the enzyme undergoes a conformational change comprises a fluorescent label whose fluorescence is sensitive to changes in its local environment. In some embodiments the signal that changes when the enzyme undergoes a conformational change comprises quenching of a fluorescent label. In some embodiments the polymerase enzyme has both a fluorescent label and a quencher attached to different portions of the enzyme, and the quenching results from relative motions of the different portions of the enzyme from a conformational change.

In some embodiments the polymerase enzyme comprises a DNA polymerase or an RNA polymerase. In some embodiments the template comprises DNA or RNA. In some embodiments the polymerase is a modified Type B polymerase.

In some embodiments the conformational change comprises translocation, or opening/closing of the fingers domain. In some embodiments at least one label is attached to the fingers, palm, thumb, or exo domains.

In one aspect, the invention provides a method for nucleic acid sequencing comprising: providing a reaction mixture for nucleic acid polymerization comprising four types of nucleotides or nucleotide analogs, each having a different label; contacting the reaction mixture with a polymerase enzyme complex comprising a polymerase enzyme, a template nucleic acid, and a primer; under conditions whereby enzyme mediated addition of nucleotides to produce a growing nucleic acid strand from the primer occurs, wherein the enzyme comprises a label which exhibits a change in optical properties when the enzyme undergoes a conformational change; observing optical signals from the nucleotides or nucleotide analog and the enzyme while the nucleotides or nucleotide analogs are incorporated into the growing nucleic acid strand; determining, using the observed optical signal from the nucleotides or nucleotide analogs, when a particular type of nucleotide or nucleotide analog is associated with the enzyme; determining, using the observed optical signal, when the enzyme undergoes a conformational change; using the determination of when a particular nucleotide or nucleotide analog is associated with the enzyme in combination with the determination of when the enzyme undergoes conformational change to determine a nucleic acid sequence of the template.

In some embodiments the labels for the enzyme and for the nucleotides or nucleotide analogs comprise fluorescent labels. In some embodiments the signal that changes when the enzyme undergoes a conformational change comprises a FRET signal from a donor and an acceptor. In some embodiments the donor and acceptor are both attached to the polymerase enzyme. In some embodiments the donor and acceptor are attached to portions of the enzyme which move relative to one another during a conformational change.

In some embodiments the label whose signal changes when the enzyme undergoes a conformational change comprises a fluorescent label whose fluorescence is sensitive to changes in its local environment. In some embodiments the signal that changes when the enzyme undergoes a conformational change comprises the quenching of a fluorescent label. In some embodiments the polymerase enzyme has both a fluorescent label and a quencher attached to different portions of the enzyme, and the quenching results from relative motions of the different portions of the enzyme from the conformational change.

In some embodiments the polymerase enzyme comprises a DNA polymerase or an RNA polymerase. In some embodiments the template comprises DNA or RNA. In some embodiments the polymerase is a modified Type B polymerase.

In one aspect, the invention provides, a system for sequencing comprising: a substrate comprising a plurality of single polymerase enzyme complexes each comprising a polymerase enzyme, a nucleic acid template, and a primer; wherein the polymerase enzyme comprises a label which has a signal that changes when the enzyme undergoes a conformational change, wherein the substrate comprising the complexes is in contact with sequencing reagents including two or more types of nucleotides or nucleotide analogs, each labeled with a different label, whereby enzyme mediated addition of nucleotides or nucleotide analogs to the primer to produce a growing strand complementary to the template occurs; illumination optics for illuminating the enzyme complexes; detection optics for observing signals from the labeled nucleotides or nucleotide analogs and signals from the labeled enzyme during the enzyme mediated addition; and a computer configured to determine the type of the nucleotides or nucleotide analog that is added to the growing strand using the observed signal from the label of the nucleotide or nucleotide analogs; whereby observed signals from the labeled polymerase enzyme are used to indicate whether a type of nucleotide or nucleotide analog is incorporated into the growing strand.

In some embodiments the substrate comprises a plurality of optical confinements, and wherein at least some of the plurality of optical confinements comprise a single active polymerase enzyme complex. In some embodiments the optical confinements comprise zero mode waveguides. In some embodiments the labels for the enzyme and the nucleotides or nucleotide analogs comprise fluorescent labels.

In some embodiments the signal that changes when the enzyme undergoes a conformational change comprises a FRET signal from a donor and an acceptor. In some embodiments the donor and acceptor are both attached to the polymerase enzyme. In some embodiments the donor and acceptor are attached to portions of the enzyme which move relative to one another during a conformational change. In some embodiments the label whose signal changes when the enzyme undergoes a conformational change comprises a fluorescent label whose fluorescence is sensitive to changes in its local environment.

In some embodiments the signal that changes when the enzyme undergoes a conformational change comprises quenching of a fluorescent label. In some embodiments the polymerase enzyme has both a fluorescent label and a quencher attached to different portions of the enzyme, and the quenching results from relative motions of the different portions of the enzyme from a conformational change.

In some embodiments the polymerase enzyme comprises a DNA polymerase or an RNA polymerase. In some embodiments the template comprises DNA or RNA. In some embodiments the polymerase is a modified Type B polymerase.

In some embodiments the conformational change comprises translocation, opening of the fingers domain, or closing of the fingers domain. In some embodiments at least one label is attached to the fingers, palm, thumb, or exo domains.

DETAILED DESCRIPTION OF THE INVENTION

General

Figure 1:
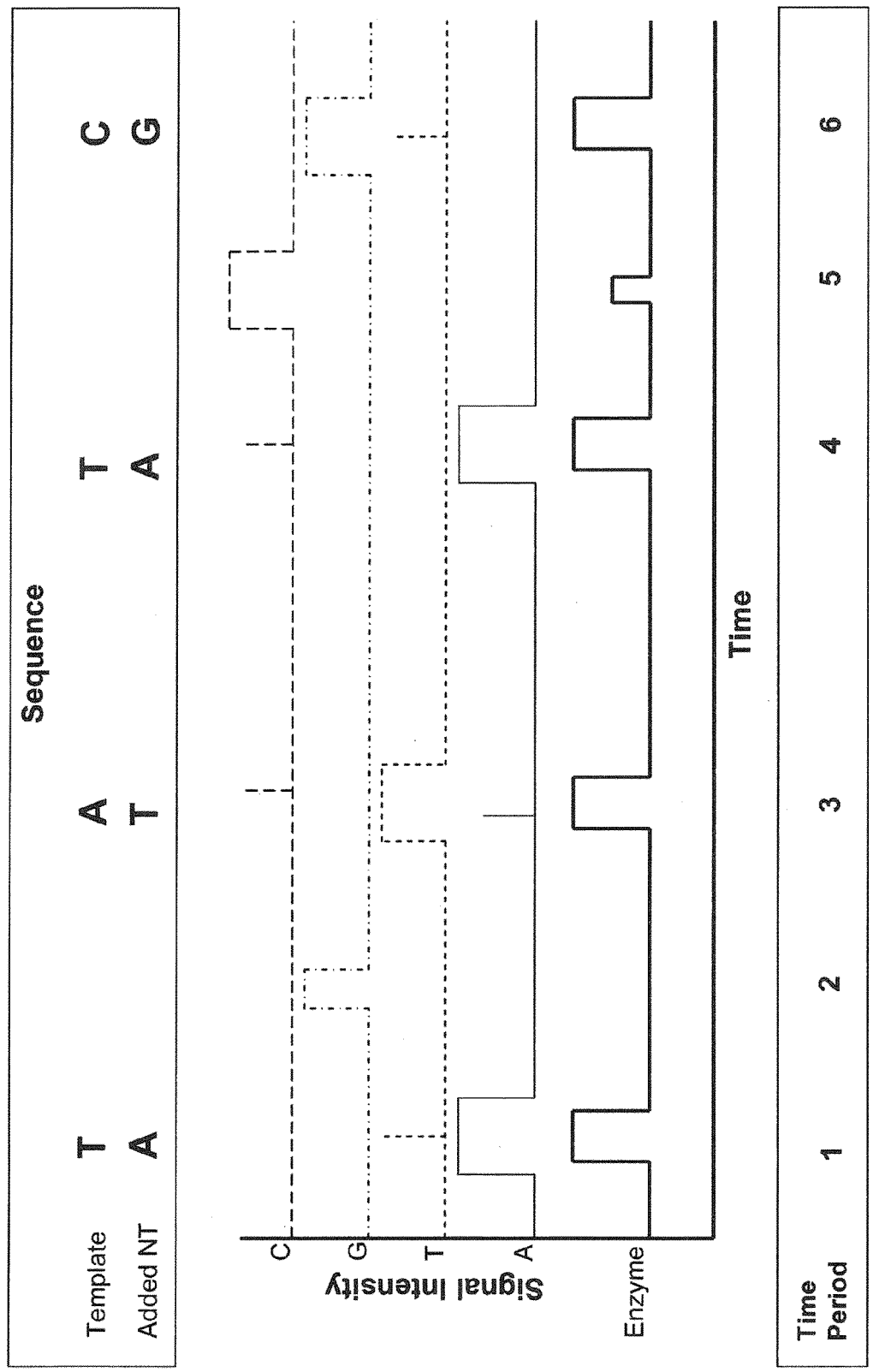
FIG. 1 illustrates observed signals from labeled nucleotides and labeled polymerase enzyme for an enzyme conformational change which occurs during the same time as nucleotide association with the polymerase (e.g. a FRET signal sensitive to open-closed conformation where the FRET pair are closer in the closed conformation).

The invention is generally directed to methods and methods for sequencing nucleic acids. In particular, the invention is directed to real-time single-molecule sequencing of nucleic acids. For example, the sequence of a template nucleic acid can be determined by observing a single nucleic acid polymerase enzyme as it grows a nascent strand complementary to the template nucleic acid. This can be accomplished by observing the addition of differentially labeled nucleotides into the growing strand by the enzyme. Since each differentially labeled nucleotide carries a distinct label, the identity of the nucleotide that is being added can be determined by observing the labeled nucleotide while it associates with the enzyme. For example, a nucleotide which becomes incorporated may spend more time associated with the enzyme than a nucleotide which does not become incorporated, allowing for calling incorporated bases based on pulse duration or other pulse characteristics. It has been demonstrated that such systems can be used to sequence DNA templates (see e.g. Eid et al. Science, 323, 133-138, 2009). While such systems have been shown to provide high accuracy, e.g. greater than 99% with 15 fold coverage (Eid et al. Science, 323, 133-138, 2009), it is desirable to have even higher accuracy. One contributor to errors in the calling of bases when carrying out such sequencing, is from pulses which have the characteristics of an incorporation pulse, yet are not due to the incorporation of a nucleotide. For example, when a pulse attributable to a labeled nucleotide is used to indicate whether a nucleotide has been incorporated, there can be cases in which a nucleotide spends a relatively long time in the active site, but is then released rather than being incorporated. Where this occurs, the event can be incorrectly identified as the incorporation of a nucleotide, resulting in an error in the determination of the sequence. These events are sometime referred to as branching events.

Alternatively, there may be cases where a labeled nucleotide adheres non-specifically to a region near the polymerase enzyme for a relatively long period of time. Again, the pulse that results from this non-specific adhesion may be called as a nucleotide incorporation, resulting in an error in sequence determination. In addition, the optical system may detect pulses which are mistakenly called as nucleotide incorporation due to noise within the system. These pulses, which have the characteristics of a pulse due to an incorporated nucleotide, but do not actually represent an incorporated nucleotide are sometimes referred to as "sticks".

The current invention provides improved sequencing accuracy by concurrently observing polymerase enzyme conformation and nucleotide addition. The polymerase enzyme undergoes a series of conformational changes during the process of adding a nucleotide to a growing strand. During these conformational changes, various regions or domains of the enzyme can move relative to one another. It has been recently shown that such conformational changes can be observed in real time, even at the single-molecule level. By observing conformational changes in the polymerase enzyme in real time while the enzyme is incorporating nucleotides, it is possible to distinguish true incorporation events from other events which might otherwise be mistaken as incorporation events.

For example, translocation of the template nucleic acid will generally only occur after the incorporation of a new nucleotide into the growing strand. By observing a signal that is characteristic of a change in enzyme conformation associated with translocation, one can obtain a direct measurement of whether nucleotide incorporation has occurred. When this is combined with the observation of the optical signals from differentially labeled nucleotides, a system is obtained which provides an accurate method nucleotide sequencing. The errors described above associated with branching and sticks can be reduced or substantially eliminated by using a translocation signal to ensure that the signal observed is associated with a true incorporation event. In addition to translocation, there are other enzyme conformational changes that can be used as an indication that true incorporation has occurred.

The signal from enzyme conformational change can be used to decide whether to include a given pulse which otherwise has characteristics associated with an incorporated nucleotide. In some cases, the presence of a signal due to an enzyme conformational change can be used to include a pulse as a base call, and the absence of a signal used to eliminate a pulse as a base call. In other cases, the presence or absence of a signal due to an enzyme conformational change can be used as one piece of information in the overall determination of whether a measured pulse is assigned as an incorporation of that nucleotide. For example, there may be instances where a pulse has characteristics indicating that it represents an incorporation event and the characteristics are strong enough such that the pulse will be called as an incorporation whether or not an enzyme conformation event has been observed, but where a pulse has characteristics that are not as strongly indicative of incorporation, the presence or absence of a signal due to enzyme conformational change will be invoked to make the call as to whether an incorporation event has occurred.

The systems and methods of the invention can use pairs of labels which have interactions which depend on distance, such as fluorescence resonance energy transfer (FRET) or quenching. The systems and methods do not require that there be an optical interaction such as FRET or quenching between an incoming labeled nucleotide. The signal corresponding to enzyme conformation is generally independent of the signals from the labeled nucleotides or nucleotide analogs. In this way, the signal from the nucleotides and nucleotide analogs can be used to indicate which type of nucleotide or nucleotide analog is interacting with the enzyme, and the signal from the labeled enzyme can be used as an indication of whether incorporation of that type of nucleotide or nucleotide analog occurs. Thus, the signal which is indicative of enzyme conformational change is generally in a different optical channel than the signal from any of the labeled nucleotides or nucleotide analogs.

FIG. 1 shows idealized signal output from an embodiment of the invention. For the method or systems illustrated in FIG. 1, a labeled polymerase enzyme provides a signal which rises in intensity when the enzyme undergoes a conformational change. The conformational change occurs substantially during the same time period in which the nucleotide or nucleotide analog is associated with the enzyme. Such an enzyme conformation signal could be generated, for example by a FRET donor and acceptor pair which are connected to portions of the enzyme that are moved farther apart when the enzyme moves into an open position, and that move closer together when the enzyme moves into a closed position. This type of enzyme labeling can be accomplished, for example, by placing one of the FRET pair on a finger region of the enzyme, and placing the other one of the FRET pair on the palm region of the enzyme. Such a system is described in Allen et al. Protein Science, 17, 401-408 (2008). The output from the acceptor fluorophore in such a FRET pair can be used to provide an indication that incorporation of a nucleotide or a nucleotide analog is occurring.

To obtain the types of signals shown in FIG. 1 an enzyme complex comprising a polymerase enzyme, a template nucleic acid, and a primer hybridized to the template nucleic acid is provided for observation. The enzyme complex is generally immobilized onto the surface either through attachment to the enzyme, primer, or the template. In some cases, the enzyme complex is immobilized within an optical confinement such as a zero mode waveguide. The enzyme complex is arranged on the surface such that a single enzyme complex can be observed. To the enzyme complex is added sequencing reagents, generally including a buffer and cofactors for carrying out the polymerase reaction. The sequencing reagents include nucleotides or nucleotide analogs, generally including four nucleotide analogs, each corresponding to A, G, C, T or A, G, C, U. In the system shown in FIG. 1, four nucleotide analogs corresponding to A, G, C, and T are provided which are each labeled with a distinct fluorescent tag or label. The tag is generally provided in a manner in which the tag is removed from the nucleotide or nucleotide analog after incorporation, for example by having the tag attached to a phosphate on the nucleotide that is cleaved upon incorporation. Such a tag can be attached, for example, to the beta, gamma, delta, epsilon, or later phosphate on a nucleic acid or nucleotide analog. By having a tag that is removed upon incorporation of the nucleotide into the growing strand, a signal from the fluorescent tag will be observed while the nucleotide is associated with the enzyme complex, and a signal from the fluorescent tag will not be observed after the tag is removed, and rapidly diffuses from the observation region that includes the enzyme complex. In this manner pulses or peaks are observed which correspond to a nucleotide or nucleotide analog associating with the active site of the enzyme, and being incorporated into the growing strand.

In addition to peaks from incorporated nucleotides, in some cases, peaks will be observed from non-incorporation events. Non-incorporation peaks may arise, for example, from nucleotides or nucleotide analogs that diffuse in and out of the observation volume, nucleotides or nucleotide analogs that non-specifically bind to a surface within the observation region, non-cognate nucleotides that sample the active site, but are not incorporated, and cognate nucleotides which enter the active site, but are released before incorporation. When a pulse that is not an incorporation event is called as an incorporation, or where a pulse which is an incorporation is called as a non-incorporation, errors can occur in determining the sequence of the target nucleotide. In many cases, it is possible to clearly distinguish an incorporation event from a non-incorporation event by pulse characteristics such as pulse shape or pulse duration. For example, a diffusing labeled nucleotide or nucleotide analog will generally produce a signal of very short duration. However, there can be cases where it is difficult to determine whether a given pulse corresponds to an incorporation event. Contemporaneously observing a signal from a change in enzyme conformation allows for distinguishing whether a given pulse corresponds to an incorporation event.

In time period 1 in FIG. 1, a pulse is observed in the optical channel corresponding to the fluorescent label on the nucleotide analog corresponding to A. This signal can be generated, for example by a nucleotide analog which has a label attached to the portion of the nucleotide which is cleaved from the nucleotide upon incorporation. Also during time period 1, a signal is observed for an enzyme conformational change which change occurs at the same time that the nucleotide is associated with the enzyme. This conformational change can involve the enzyme moving from an open to a closed conformation, in which a FRET pair is moved close together when the enzyme enters the closed conformation, resulting in a rise in signal from the acceptor fluorophore. This set of concurrent signals from the nucleotide and the enzyme provides information that can be used to confirm that an actual incorporation of an analog of A has occurred, thus correctly identifying the base at this position of the template as a T.

In time period 2 in FIG. 1, a pulse is observed in the optical channel corresponding to the fluorescent label on the nucleotide analog corresponding to G. During time period 2, there is no signal corresponding to enzyme conformation change, thus, the peak G can be ruled out as an incorporation event or assigned a low probability of being an incorporation event. Peak G could be due, for example, to a non-specific adsorption of the nucleotide analog to a surface within the observation region, or to a non-cognate sampling of the enzyme active site.

In time period 3, a pulse is observed in the optical channel corresponding to the fluorescent label on the nucleotide analog corresponding to T. In time period 3 a signal from the label that is sensitive to enzyme conformation is also observed. This signal provides evidence that an analog corresponding to T has been incorporated, thus correctly identifying the base at this position of the template as an A.

In time period 4, a pulse is observed in the optical channel corresponding to the fluorescent label on the nucleotide analog corresponding to A. In time period 4 a signal from the label that is sensitive to enzyme conformation is also observed. This signal provides evidence that an analog corresponding to A has been incorporated, thus correctly identifying the base at this position of the template as a T.

In time period 5, a pulse corresponding to a fluorescent label on the nucleotide analog G is observed. Also in time period 5, a pulse is observed in the channel corresponding to enzyme conformation. While a signal due to conformational change is observed, the characteristics of the pulse in this case indicate that the complete conformational change has not occurred, and therefore no incorporation has occurred. This scenario illustrates the situation were not only can the presence or absence of a signal corresponding to a conformational change be used to improve base calling, but that the characteristics of the signal, such as the intensity of the signal (e.g. pulse height) or the duration of the signal (e.g. pulse width) due to conformational change can be used to assist in making the correct call on incorporation. An example of a pulse having different characteristics in the case of incorporation is conformational change from open to closed in which the closed conformation is different in the case of the association in the active site with a cognate and a non-cognate nucleotide. Observation of FRET labeled polymerase enzymes has indicated that there may be a weaker signal for the closed/open conformation when a non-cognate nucleotide is associated with a polymerase enzyme than when a cognate nucleotide is associated (Allen et al. Protein Sci 17(3): 401-8, 2008).

In time period 6, a pulse is observed in the optical channel corresponding to the fluorescent label on the nucleotide analog corresponding to G. In time period 6 a signal from the label that is sensitive to enzyme conformation is also observed. This signal provides evidence that an analog corresponding to G has been incorporated, thus correctly identifying the base at this position of the template as a C.

Thus, as shown in FIG. 1, the methods and systems of the invention can be used to accurately determining the sequence of a template nucleotide by concurrently observing in real time both the addition of labeled nucleotides or nucleotide analogs, and the signal from a label that is sensitive to a conformational change.

Note that short pulses are observed in the T channel of time period 1, the A and C channels of time period 3, the C channel of time period 4, and the T channel of time period 6. While these pulses do correspond to time periods in which the enzyme conformational change occurs, these events can be ruled out or given low probability as incorporation event because of the characteristics of the pulse. Here, such a short duration pulses identifies the pulses as a non-incorporation events.

Figure 2:
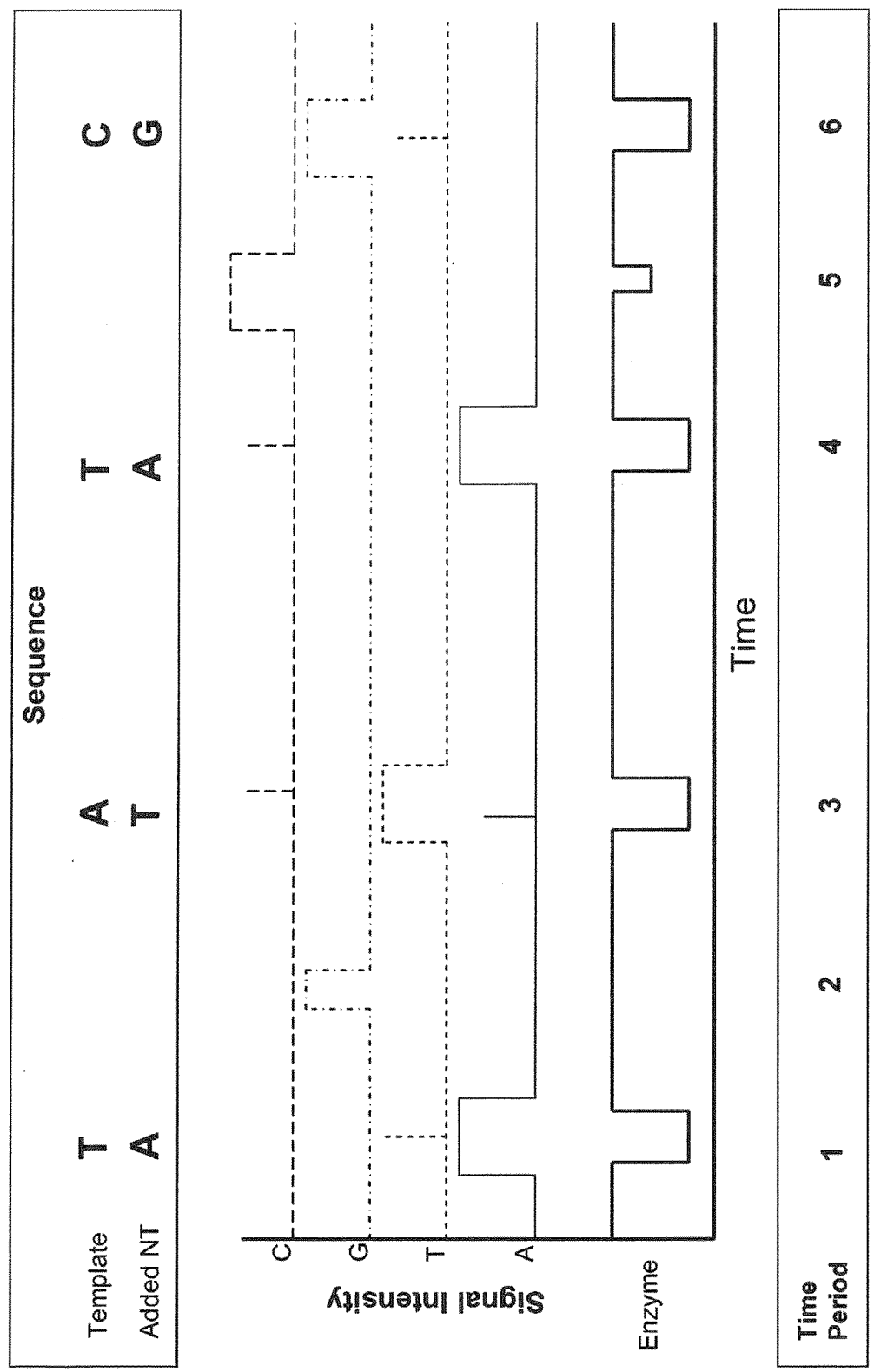
FIG. 2 illustrates observed signals from labeled nucleotides and labeled polymerase enzyme for an enzyme conformational change which occurs during the same time as nucleotide association with the polymerase (e.g. a quenched signal sensitive to open-closed conformation where the donor-quencher pair are closer in the closed conformation).

FIG. 2 illustrates a sequencing method and system similar to that shown in FIG. 1 where the enzyme signal shows a decrease in intensity during a conformational that corresponds with nucleotide incorporation. A system having these characteristics can be obtained, for example, by having each of a fluorescent dye and a quencher attached to different portions of an enzyme. For example, signals with these characteristics can be obtained with a polymerase enzyme having the fluorescent dye and the quencher each attached to portions of the enzyme which come together when the enzyme enters a closed conformation, and which come apart when the enzyme enters into an open conformation. For example, a fluorescent dye is attached to the finger domain of the enzyme and a quencher for the dye attached to the palm domain of the enzyme. When the enzyme is in the open conformation, the dye and quencher are farther apart, and the signal intensity from the fluorescent dye is high. When the enzyme enters the closed conformation as a cognate nucleotide is incorporated, the fluorescent dye and the quencher are brought closer together, resulting in quenching of the fluorescent dye, and a lowering of the signal.

Thus, analogous to the discussion above relating to FIG. 1, for FIG. 2 in periods 1, 3, 4, and 6 a signal corresponding to the addition of the correct nucleotide analog is detected, and in the corresponding time period, a drop in signal is observed indicative of an enzyme conformational change providing corroborating evidence that the identified nucleotide analog was incorporated. In time period 2, a pulse in the channel corresponding to label on the nucleotide analog G is detected. During time period 2, no signal corresponding to enzyme conformational change is seen, indicating that the pulse in the G channel did not represent a nucleotide incorporation. In time period 5, a pulse in the channel representative of the nucleotide analog corresponding to C is observed. While a signal corresponding to an enzyme conformational change is seen, the characteristics of the signal can be differentiated from the signal from a conformational change that results in incorporation. For example, the intensity of the signal, the duration of the signal, and the shape of the signal can be used to differentiate a conformational change that leads to incorporation and one that does not. For example, where the monitored enzyme conformation is the opening and closing of a polymerase, a difference in the amount of quenching can be observed when a non-cognate nucleotide is in the active site than when a cognate nucleotide is in the active site where, for example, the closing of the enzyme is more complete in the case of a cognate nucleotide. Thus, the signal corresponding to C in time period 5 can be eliminated or given a low probability of corresponding to an incorporation event.

Figure 3:
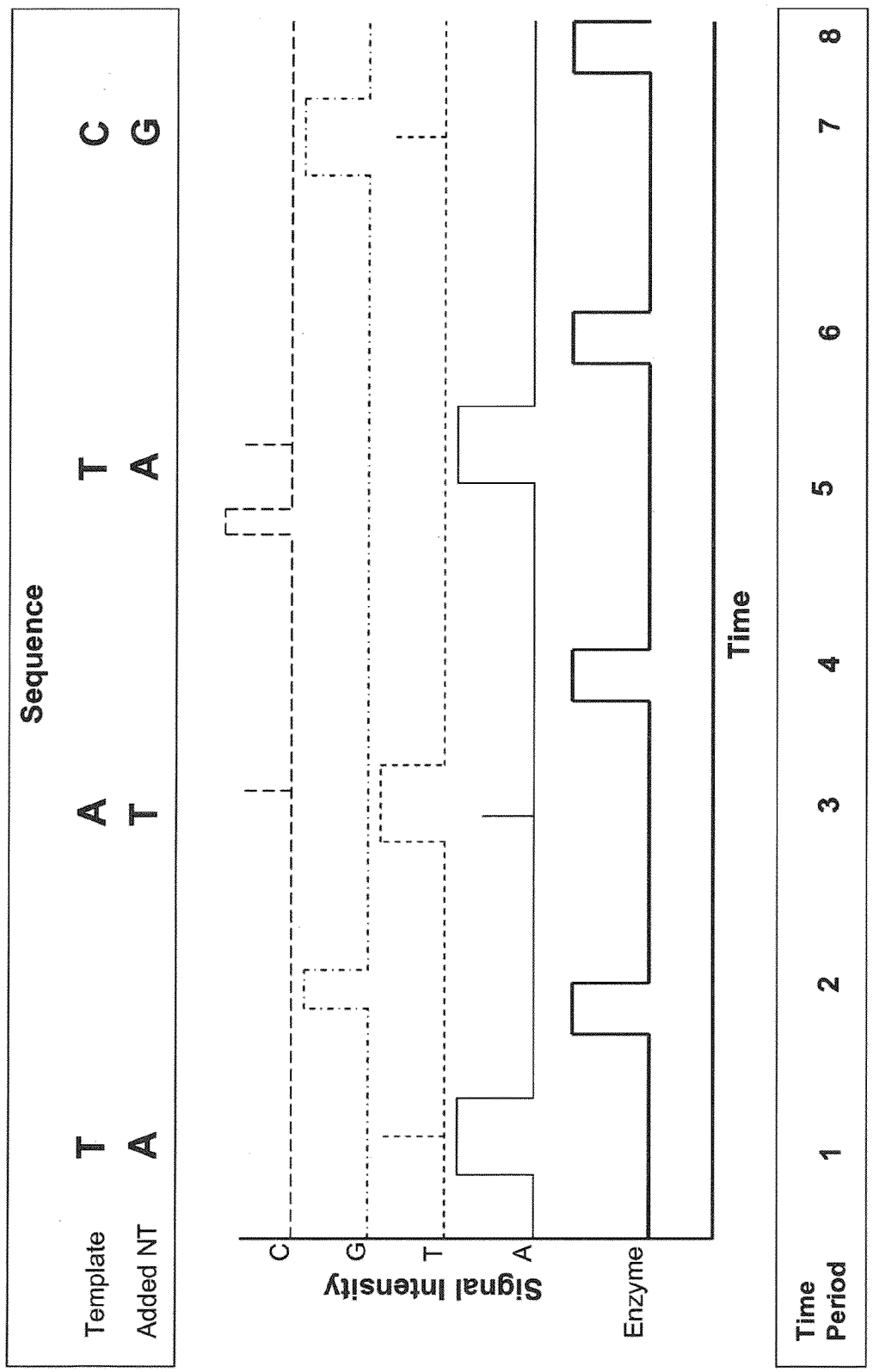
FIG. 3 illustrates observed signals from labeled nucleotides and labeled polymerase enzyme for an enzyme conformational change which occurs at a different time in the catalytic cycle from nucleotide association with the polymerase (e.g. a FRET signal from an enzyme conformational change indicative of a translocation event).

FIG. 3 illustrates the output from a method or system in which the enzyme conformational change which is monitored indicates that an incorporation has occurred, and the conformational change does not occur at the same time as the addition of the nucleotide. Such a system is seen, for example, where the monitored enzyme conformational change is translocation. Translocation occurs after the addition of a nucleotide to the growing strand when the template nucleotide moves down one base in order to allow for the addition of a nucleotide to the next base position. The observation of a translocation event indicates that a single nucleotide has been incorporated. The translocation event can be, for example, the change in the conformation of the polymerase corresponding to the flipping out of the base in the minus-one position. See, for example, Joyce et al. Biochim Biophys Acta. doi:10.1016/j.bbapap.2009.07.021. FRET between a donor and acceptor attached to positions on the enzyme which move relative to one another during this transition, or the FRET between a tag attached to the polymerase and a base on the template can result in a reproducible signal characteristic of translocation. For the system of FIG. 3, the label on the enzyme exhibits a rise, then a fall in intensity during translocation.

In time period 2, a translocation event is observed. Prior to time period 2, in time period 1, a pulse due to the label corresponding to nucleotide analog A is observed. The translocation event at time period 2 indicates that the A pulse is a true incorporation, and that the enzyme is now in position for another nucleotide addition. In time period 4, another translocation event is observed. Between the translocation events at time period 2 and time period 4, a pulse in the channel corresponding to the label on the nucleotide analog of T is observed. The observation of the translocation signals helps to confirm that the T is the base that was incorporated. While a signal in the channel for the label on the nucleotide analog corresponding to G is seen in time period 2, the timing of the pulse, as overlapping with the time frame of translocation can be used to eliminate that pulse as representing an incorporation.

In time period 6, another translocation event is observed in the channel corresponding to changes in enzyme conformation. In the time period between the two translocation events, a signal from the label on the nucleotide analog corresponding to A and a signal from the label on the nucleotide analog corresponding to C are observed. The observation of the translocation event at time period 6 indicates that only one nucleotide has been incorporated in this time period. Other information about the A and the C pulse can then be used to call the correct base. Information such as pulse width, pulse height, pulse shape, and the timing of the pulse between translocation events can be used. In addition, information about the relative timing of the pulses and a measure of where the pulse falls between the two translocation events can be used to indicate true incorporation. For example, for a series of events corresponding to a nucleotide interacting with the active site, sampling prior to incorporation, the last event will be the incorporation event. In addition, in some cases where the pulse falls in relation to the two translocation events can be used to indicate incorporation. In some cases, for example, it will be expected that the pulse from the nucleotide which is incorporated will occur right before the subsequent translocation event, therefore occurring closer to the translocation event after the pulse than the translocation before the pulse. Here this information is used to correctly call A as the incorporated base. In time period 8, another translocation event is observed. This event indicates that one incorporation has occurred between time periods 6 and 8, and is used to confirm that the pulse from the label on the nucleotide analog corresponding to G represents incorporation of G. Thus, the enzyme signal from translocation is used to provide information about the timing of incorporation events, which is then used to improve the accuracy of sequencing.

Single Molecule Sequencing

For sequencing processes that rely upon monitoring of the incorporation of nucleotides into growing nascent strands being synthesized by the complex, the progress of the reaction through these steps is of significant importance. In particular, for certain "real time" nucleotide incorporation monitoring processes, the detectability of the incorporation event is improved based upon the amount of time the nucleotide is incorporated into and retained within the synthesis complex during its ultimate incorporation into a primer extension product.

By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, 2003, and Eid et al. Science, 323, 133-138, 2009, the full disclosures of which are incorporated herein by reference in their entirety for all purposes.

Figure 4:
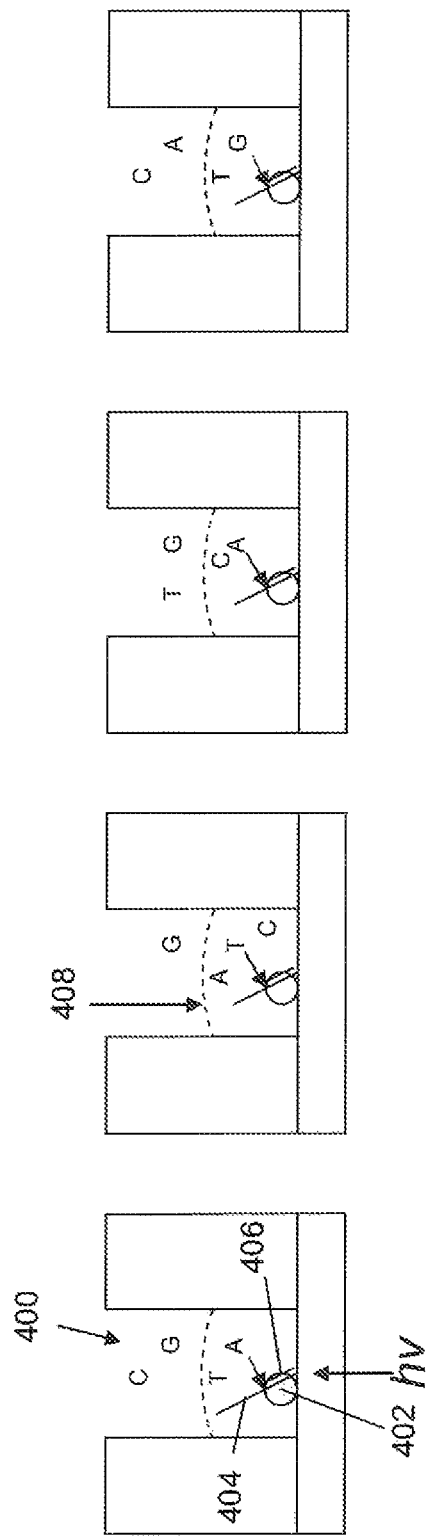
FIG. 4 provides a schematic drawing showing single molecule sequencing within an optical confinement.

In an exemplary technique, as schematically illustrated in FIG. 4, a nucleic acid synthesis complex, including a polymerase enzyme 402, a template sequence 404 and a complementary primer sequence 406, is provided immobilized within an observation region 400, that permits illumination (as shown by hv) and observation of a small volume that includes the complex without excessive illumination of the surrounding volume (as illustrated by dashed line 408). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

In particularly preferred exemplary systems, the confined illumination volume is provided through the use of arrays of optically confined apertures termed zero mode waveguides, e.g., as shown by confined reaction region 400, (ZMWs) (See, e.g., U.S. Pat. No. 6,917,726, which is incorporated herein by reference in its entirety for all purposes). For sequencing applications, the DNA polymerase is provided immobilized upon the bottom of the ZMW (See, e.g., Korlach et al., PNAS U.S.A. 105(4): 1176-1181. (2008), which is incorporated herein by reference in its entirety for all purposes.

In operation, the fluorescently labeled nucleotides (shown as A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuse away from the complex following incorporation of the associated nucleotide, nor do such labels interfere with the incorporation event. See, e.g., Korlach et al., Nucleosides, Nucleotides and Nucleic Acids, 27:1072:1083, 2008.

In another exemplary technique, the immobilized complex and the nucleotides to be incorporated are each provided with interactive labeling components. Upon incorporation, the nucleotide borne labeling component is brought into sufficient proximity to the complex-borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

Method with 5 Optical Channels

One aspect of the invention is a method in which signals in five or more optical channels are measured simultaneously in order to perform sequencing on a template nucleic acid. Four of the signals are from labels on each of four nucleotides or nucleotide analogs, and one signal is a signal indicative of a conformational change of a polymerase enzyme from a label on the polymerase enzyme. The labels are chosen such that the 5 signals are separately resolvable within the same time period during which they are observed. For example, the fluorescence emission maxima of 5 fluorescent dyes are chosen such that all 5 can be separately determined in the presence of each other. The method is generally carried out under single-molecule observation conditions in which the action of a single polymerase adding nucleotides or nucleotide analogs to a growing strand is monitored. The method generally utilizes a polymerase enzyme complex which is immobilized to a surface, either by attachment of the enzyme, the primer, or of the template nucleic acid to the surface. Typically the method is performed on multiple enzyme complexes simultaneously whereby each of the polymerase reactions can be separately observed, providing a means of multiplex sequencing. The polymerase enzyme complexes can be disposed within an optical confinement structure such as a zero mode waveguide to enhance detection and lower background signal.

The polymerase enzyme complex is in contact with polymerase reagents including buffer, metal ions, and the four labeled nucleotides. These components are present in concentrations sufficient to sustain a polymerase reaction. Where nucleotides having terminal phosphate labels, or labels which are cleaved upon incorporation, a pulse corresponding to a particular nucleotide or nucleotide analog will be observed when the nucleotide or nucleotide analog is associated with the polymerase enzyme, such as when the nucleotide analog is within the active site. Where the nucleotide is incorporated, the label will be cleaved, and will diffuse from the observation volume resulting in the end of the pulse. While some background signal from nucleotide analogs in solution will be present, the signal can generally be distinguished from the pulses due to association of the nucleotide analog with the enzyme, for example by pulse duration.

Figure 5:
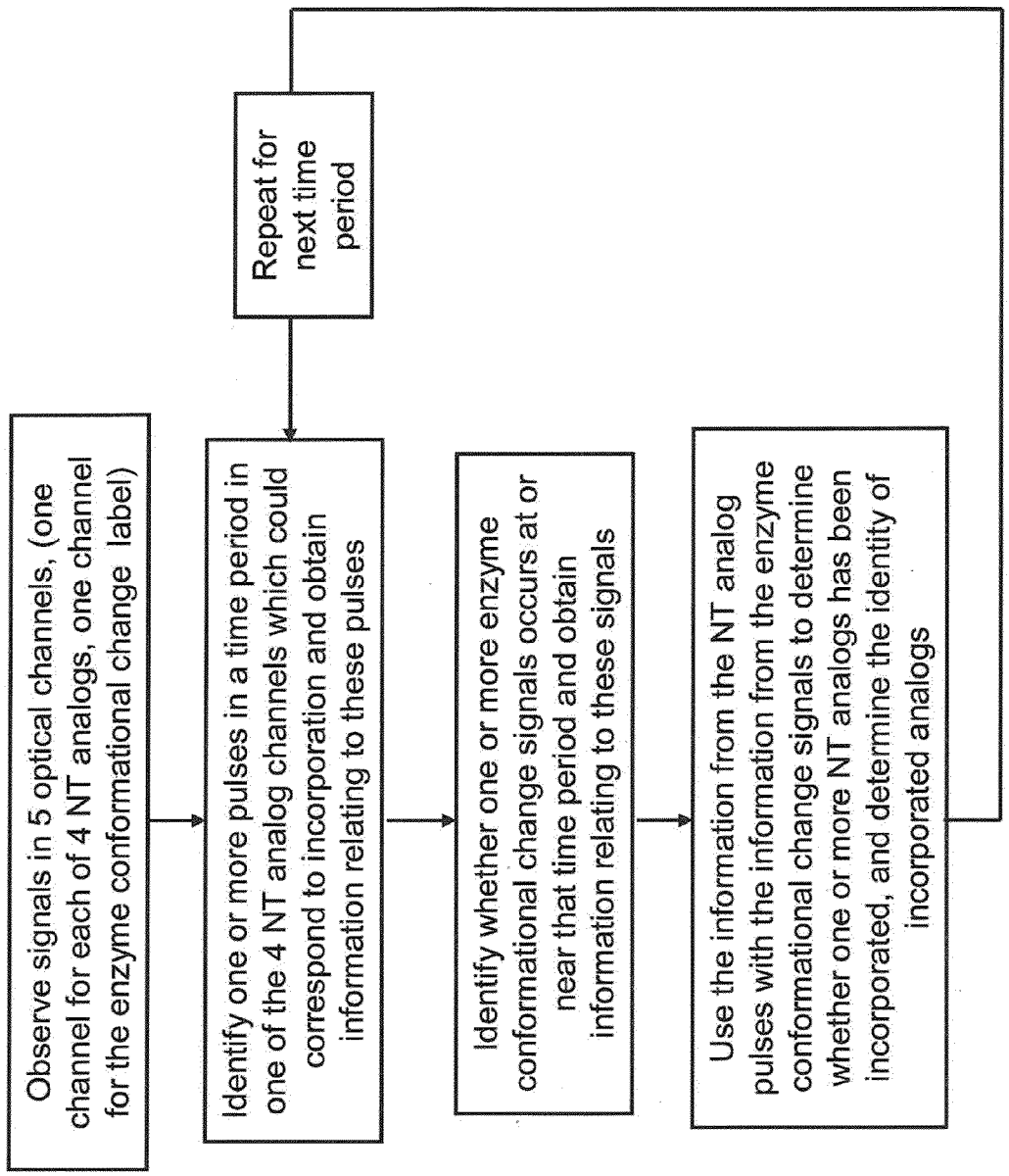
FIG. 5 is a flow chart illustrating an embodiment of a process of the invention for sequencing a template nucleic acid.

FIG. 5 shows a flow chart illustrating an embodiment of the invention. The five optical signals are observed over time. The detection system can have 5 distinguishable channels. Within a given time period, one or more pulses is identified within one or more of the NT analog channels which may correspond to an incorporation event. Information relating to the identified pulses is obtained. Concurrently, in the enzyme conformation signal channel, signals or pulses are identified which may correspond to the conformational change which is being monitored. In some cases, no signals or pulses will be identified at or near the time period. Information is then obtained on any signals that are identified. The information from the nucleotide analog pulses and the information from the enzyme conformation signals is then used to determine whether one or more incorporation events has occurred, and if a nucleotide event has occurred, the identity of the incorporated nucleotide. The information that is used can include intensity, frequency, intensity vs. frequency, pulse width, pulse shape, etc. This process can then be repeated for another time period. The enzyme conformation signals allow for a more accurate determination of whether incorporation has occurred than if the same sequencing reaction was carried out without measuring the enzyme conformation signals. While FIG. 5 provides one set of steps, other sets of steps will be apparent for carrying out the methods of the invention for using enzyme conformational change signals along with labeled nucleotide analog signals to obtain accurate sequence information than if the sequence was determined without using the enzyme conformation signals.

Where five or more signals are monitored simultaneously, generally the 5 or more labels that are monitored will each provide optical signal in a different portion of the spectrum. Sets of fluorescent dyes are known which can be used in combination such that there is a small enough overlap in their emission spectra such that the 5 dyes can be used together. Generally, the 5 dyes will all be excited and will emit in the visible spectrum. In some cases excitation and emission in the UV or infrared can be used. In some cases characteristics other than or in addition to spectral differences can be used to differentiate the dyes. For example, polarization or fluorescent lifetime can be used. In some cases, the labels are fluorescent labels and each label is excited at a different range of wavelengths, e.g. with five separate lasers. In some cases, one excitation source is used, e.g. one laser. In some cases, two, three, or four excitation sources are used. It can be desirable to have two separate lasers, one exciting two of the fluorescent labels, the other exciting the other three labels.

Labels on the Nucleotide or Nucleotide Analog

As discussed, various polymerases of the invention can incorporate one or more nucleotide analogs into a growing oligonucleotide chain. Upon incorporation, the analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" (or "nucleotide analogue") herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue. The systems and methods of the invention are generally applicable to either nucleotides or nucleotide analogs. Where the specification describes methods using nucleotides, unless it is specifically stated, it is to be understood that such method can also be used with nucleotide analogs.

In one useful aspect of the invention, nucleotide analogs can also be modified to achieve any of the improved properties desired. For example, various linkers or other substituents can be incorporated into analogs that have the effect of reducing branching fraction, improving processivity, or altering rates. Modifications to the analogs can include extending the phosphate chains, e.g., to include a tetra-, penta-, hexa- or heptaphosphate group, and/or adding chemical linkers to extend the distance between the nucleotide base and the dye molecule, e.g., a fluorescent dye molecule. Substitution of one or more non-bridging oxygen in the polyphosphate, for example with S or $BH_3$, can change the polymerase reaction kinetics, e.g., to achieve a system having two slow steps as described herein below. Optionally, one or more, two or more, three or more, or four or more non-bridging oxygen atoms in the polyphosphate group of the analog has a sulfur (S) substituted for an oxygen (O). While not being bound by theory, it is believed that the properties of the nucleotide, such as the metal chelation properties, electronegativity, or steric properties, can be altered by substitution of the non-bridging oxygen(s).

Many nucleotide analogs are available and can be incorporated by the polymerases of the invention. These include analog structures with core similarity to naturally occurring nucleotides, such as those that comprise one or more substituent on a phosphate, sugar or base moiety of the nucleoside or nucleotide relative to a naturally occurring nucleoside or nucleotide. In one embodiment, the nucleotide analog includes three phosphate containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate. For example, a variety of nucleotide analogs that comprise, e.g., from 4-6 or more phosphates are described in detail in U.S. patent application Ser. No. 11/241,809, filed Sep. 29, 2005, and incorporated herein by reference in its entirety for all purposes. Other exemplary useful analogs, including tetraphosphate and pentaphosphate analogs, are described in U.S. Pat. No. 7,041,812, incorporated herein by reference in its entirety for all purposes.

For example, the analog can include a labeled compound of the formula:

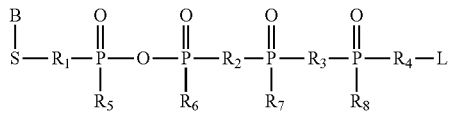

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), C($CH_2$), $CNH_2$, $CH_2CH_2$, C(OH)$CH_2$R where R is 4-pyridine or 1-imidazole, provided that $R_4$ may additionally be selected from

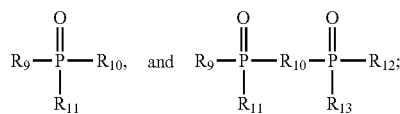

$R_5$, $R_6$, $R_7$, $R_8$, $R_{11}$ and $R_{13}$ are, when present, each independently selected from O, $BH_3$, and S; and $R_9$, $R_{10}$ and $R_{12}$ are independently selected from O, NH, S, methylene, substituted methylene, $CNH_2$, $CH_2CH_2$, C(OH)$CH_2$R where R is 4-pyridine or 1-imidazole. In some cases, phosphonate analogs may be employed as the analogs, e.g., where one of $R_2$, $R_3$, $R_4$, $R_9$, $R_{10}$ or $R_{12}$ are not O, e.g., they are methyl etc. See, e.g., U.S. patent application Ser. No. 11/241,809, previously incorporated herein by reference in its entirety for all purposes.

The base moiety incorporated into the analog is generally selected from any of the natural or non-natural nucleobases or nucleobase analogs, including, e.g., purine or pyrimidine bases that are routinely found in nucleic acids and available nucleic acid analogs, including adenine, thymine, guanine, cytidine, uracil, and in some cases, inosine. As noted, the base optionally includes a label moiety. For convenience, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogs, the S group is optionally a sugar moiety that provides a suitable backbone for a synthesizing nucleic acid strand. For example, the sugar moiety is optionally selected from a D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in U.S. Patent Application Publication No. 2003/0124576, which is incorporated herein by reference in its entirety for all purposes.

For most cases, the phosphorus containing chain in the analogs, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the $R_4$ (or $R_{10}$ or $R_{12}$ etc.) group. The labeling groups employed in the analogs of the invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, and physical labels, e.g., labels that impart a different physical or spatial property to the analog, e.g., a mass tag or molecular volume tag. In some cases individual labels or combinations may be used that impart more than one of the aforementioned properties to the analogs of the invention.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc. and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the nucleotide analogs incorporated by the polymerases of the present invention, are described in, e.g., U.S. Patent Application Publication No. 2003/0124576, previously incorporated herein by reference in its entirety for all purposes.

Additional details regarding analogs and methods of making such analogs can be found in U.S. patent application Ser. No. 11/241,809, filed Sep. 29, 2005, and incorporated herein by reference in its entirety for all purposes.

Thus, in one illustrative example, the analog can be a phosphate analog (e.g., an analog that has more than the typical number of phosphates found in nucleoside triphosphates) that includes, e.g., an Alexa dye label. For example, an Alexa488 dye can be labeled on a delta phosphate of a tetraphosphate analog (denoted, e.g., A488dC4P or A488dA4P, for the Alexa488 labeled tetraphosphate analogs of C and A, respectively), or an Alexa568 or Alexa633 dye can be used (e.g., A568dC4P and A633dC4P, respectively, for labeled tetraphosphate analogs of C or A568dT6P for a labeled hexaphosphate analog of T), or an Alexa546 dye can be used (e.g., A546dG4P), or an Alexa594 dye can be used (e.g., A594dT4P). As additional examples, an Alexa555 dye (e.g., A555dC6P or A555dA6P), an Alexa 647 dye (e.g., A647dG6P), an Alexa 568 dye (e.g., A568dT6P), and/or an Alexa660 dye (e.g., A660dA6P or A660dC6P) can be used in, e.g., single molecule sequencing. Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

Alternative labeling strategies may employ inorganic materials as labeling moieties, such as fluorescent or luminescent nanoparticles, e.g. nanocrystals, i.e. Quantum Dots, that possess inherent fluorescent capabilities due to their semiconductor make up and size in the nanoscale regime (See, e.g., U.S. Pat. Nos. 6,861,155, 6,699,723, 7,235,361). Such nanocrystal materials are generally commercially available from, e.g., Molecular Probes, (Oregon). Again, such compounds may be present as individual labeling groups or as interactive groups or pairs, e.g., with other inorganic nanocrystals or organic fluorophores.

Polymerase Mechanism

In natural polymerase mediated nucleic acid synthesis, a complex is formed between a polymerase enzyme, a template nucleic acid sequence, and a priming sequence that serves as the point of initiation of the synthetic process. During synthesis, the polymerase samples nucleotide monomers from the reaction mix to determine their complementarity to the next base in the template sequence. When the sampled base is complementary to the next base, it is incorporated into the growing nascent strand. This process continues along the length of the template sequence to effectively duplicate that template. Although described in a simplified schematic fashion, the actual biochemical process of incorporation can be relatively complex. A diagrammatical representation of the incorporation biochemistry is provided in FIG. 6. This diagram is not a complete description of the mechanism of nucleotide incorporation. During the reaction process, the polymerase enzyme undergoes a series of conformational changes which can be essential steps in the mechanism.

Figure 6:
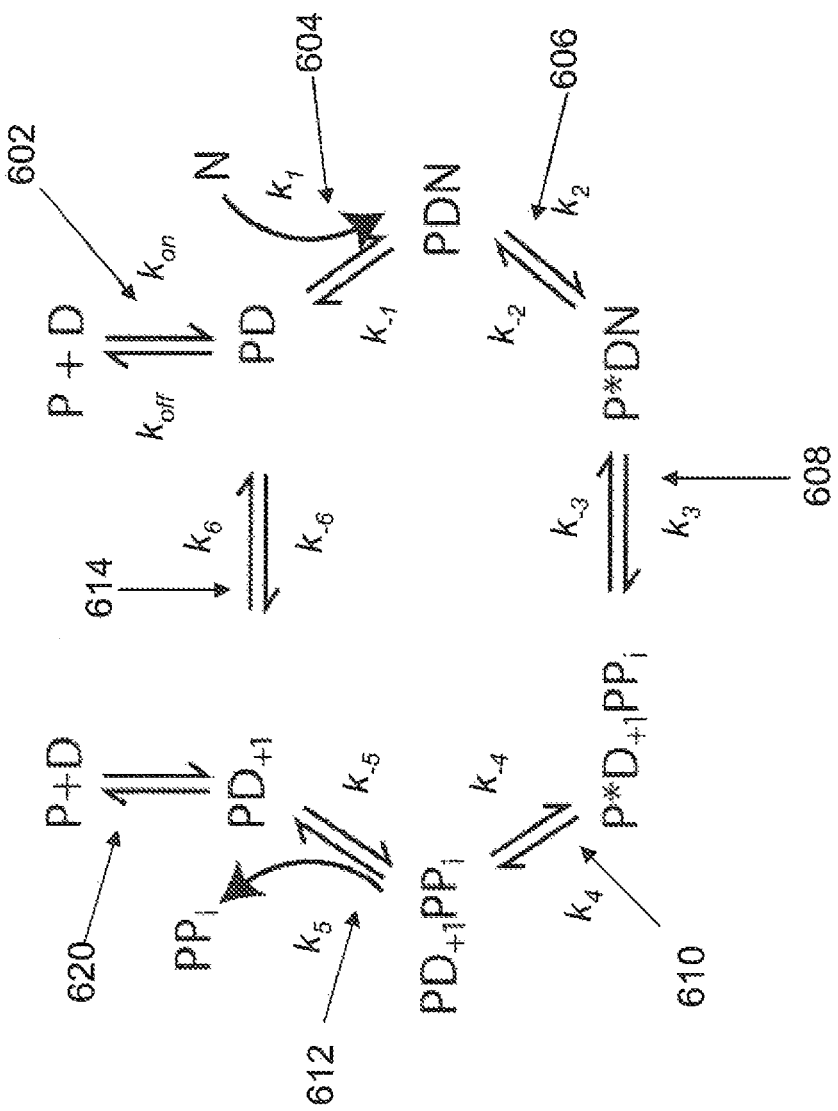
FIG. 6 shows a kinetic model of the catalytic process of nucleotide addition to a growing chain by a polymerase enzyme.

As shown in FIG. 6, the synthesis process begins with the binding of the primed nucleic acid template (D) to the polymerase (P) at step 602. Nucleotide (N) binding with the complex occurs at step 604. Step 606 represents the isomerization of the polymerase from the open to closed conformation. Step 608 is the chemistry step in which the nucleotide is incorporated into the growing strand. At step 610, polymerase isomerization occurs from the closed to the open position. The polyphosphate component that is cleaved upon incorporation is released from the complex at step 612. While the figure shows the release of pyrophosphate, it is understood that when a labeled nucleotide or nucleotide analog is used, the component released may be different than pyrophosphate. In many cases, the systems and methods of the invention use a nucleotide analog having a label on its terminal phosphate, such that the released component comprises a polyphosphate connected to a dye. The polymerase then translocates on the template at step 614. After translocation, the polymerase is in the position to add another nucleotide and continue around the reaction cycle. The reaction continues to proceed around the cycle, adding new nucleotides to the growing strand. In some cases, the polymerase will dissociate from the template in either step 620 or step 602. For a processive enzyme, the enzyme can add thousands or tens of thousands of nucleotides without dissociation. In many cases it is useful to use an enzyme which is processive for the real time sequencing of the invention.

As shown, the various steps can include reversible paths and may be characterized by the reaction constants shown in FIG. 6 where:

$k_{on}/k_{off}$=DNA binding/release;
$k_1/k_1$=nucleotide binding/release;
$k_2/k_2$=polymerase isomerization (open/closed);
$k_3/k_3$=nucleotide incorporation (chemistry);
$k_4/k_4$=polymerase isomerization (closed/open);
$k_5/k_5$=polyphosphate release/binding;
$k_6/k_6$=polymerase translocation.

Thus, during steps 604 through 610, the nucleotide is retained within the overall complex, and during steps 604 and 606, reversal of the reaction step will yield an unproductive event, i.e., not resulting in incorporation. For example, a bound nucleotide at step 604, may be released regardless of whether it is the correct nucleotide for incorporation. Where the sequencing method comprises a nucleotide having a label which is released at step 612, for example a nucleotide having a label on its terminal phosphate, the label is associated with the enzyme from step 604 to step 612. By observing the enzyme complex, we are able to detect the label while it is associated with the enzyme during these steps. By having differentially labeled nucleotides, we can discern which nucleotide is associated with the enzyme, and thereby determine which nucleotide has been incorporated at that point in the growing nascent strand.

Conformational Changes

Polymerases are by their very nature small machines. Polymerases adopt a series of conformations as they proceed through the catalytic cycle described above. Polymerases are made up of domains, which, like the parts of a machine, can move relative to one another during the polymerase reaction. Such movement can be detected, for example using fluorescent dyes either sensitive to local environment or sensitive to the proximity of another label e.g. through FRET or quenching. In the current invention, we use the determination of conformational changes to provide specific information about whether or not the incorporation of a cognate nucleotide has occurred. This information is coupled with information from concurrently measured signals from differentially labeled nucleotides in order to provide information about the sequence of the template nucleotide onto which a rowing strand is polymerized. Any detectable conformational change that provides information about whether a nucleotide is being incorporated can be used. In some cases, the conformational change is one that is called out in the polymerization mechanism, for example translocation or the change from an open to a closed conformation. In other cases, the conformational change may not correspond directly to a mechanistic step as drawn in the minimal mechanism above. In some cases the measurement of a conformational change comprises measuring a signal indicating that the enzyme is adopting one or another conformation, for example, a signal indicating that the enzyme is in either the open or the closed conformation. In other cases, the signal indicating conformational change may be generated during the movement of the enzyme as it proceeds from one conformation to another.

Some polymerases contain exonuclease domains. Conformational changes related to exonuclease activity can also be used to improve accuracy by indicating when an exonuclease proof reading event has occurred. In addition, movements of the exonuclease domain relative to other domains such as the fingers, palm, and thumb domains can provide a measurement of other conformational changes, such as translocation. In some cases, a polymerase may adopt one conformation which has high accuracy, and another conformation for which the accuracy is low. By monitoring which conformation that the enzyme is adopting, increased sequencing accuracy can be obtained. For example, a higher weight can be given to bases called during the high accuracy conformation.

Translocation

In one aspect of the invention, the conformational change that is observed using one or more labels attached to the enzyme comprises translocation. Translocation provides a useful conformational change signal because observation of the event of translocation is indicative that just prior to translocation an incorporation event has occurred. As described above in FIG. 3, the measurement of translocation can assist in making the correct determination of which nucleotide has been added to the growing strand. For example, where sequencing is performed by monitoring the signal from 4 differentially labeled nucleotides as the polymerase reaction proceeds, in some cases a signal will be seen that corresponds to a cognate or non-cognate nucleotide associating with the active site of the enzyme, but not leading to an incorporation event. In some cases, such a signal will be incorrectly identified as an incorporation, resulting in an error in the sequence. This type of error is sometimes referred to as branching. The observation of a signal due to translocation allows for differentiating a branching event from an incorporation event. A branching event will not be followed by translocation. Thus, where multiple signals are observed between translocation events, and some are branching, the last observed signal will generally correspond to the incorporation event because it was only after this event that translocation occurred.

Another source of error is a situation where a true incorporation event leads to a relatively short and or a relatively weak pulse. If two translocation events are observed sequentially, it is expected that an incorporation event occurred between these translocation events. This information can be used to call a pulse related to a nucleotide which is observed in this interval which might otherwise be discounted, again allowing for increased accuracy.

Yet another source of error is related to pulses which have no correlation with enzyme activity, but correspond to a signal from a nucleotide analog label. These pulses can result, for example, from nucleotide analogs that bind non-specifically for a time period within the observation region. The pulses can also result from other noise within the system such as noise in the detector, or autofluorescence within the optical train. These pulses are sometimes referred to as sticks. While it is often possible to eliminate pulses due to sticks on the basis of the pulse characteristics, in some cases, the stick pulses may have characteristics which are within a range such that they are designated as an incorporation, resulting in a sequencing error. By measuring signals corresponding to translocation, the number of false calls due to sticks can also be minimized because the timing of the stick pulses will generally not correspond to incorporation events, and the translocation signal provides a measure of when the incorporation event is occurring.

It is known that replicative DNA polymerases move along the template in a processive manner. The structural basis of translocation has been characterized in for polymerases, in particular A family and B family polymerases. See, for example, Berman et al. EMBO Journal, 26(14) 3494-3505. Studies, such as described by Berman show areas of the polymerase which exhibit significant movement during translocation. For example, single-subunit replicative polymerases contain a polymerase domain divided into functional subdomains arranged in a gross common architecture likened to a right hand. The thumb and fingers subdomains form the sides of a 'U'-shaped cleft, at the bottom of which is the catalytic palm subdomain that utilizes a two-metal ion mechanism for catalyzing phosphodiester bond formation. The thumb subdomain stabilizes the primer-template duplex product and the fingers subdomain contains basic residues that bind the triphosphate moiety of the incoming nucleotide and the pyrophosphate product of the phosphoryl transfer reaction. The coordinated movements of these subdomains have been extensively studied in polymerase families, including family A (bacterial repair polymerases, most bacteriophage replicative polymerases, and T7 RNA polymerase (RNAP)) and family B (viral and eukaryotic genome replicating enzymes).

Structural studies have indicated that after binding a primer-template DNA substrate, A-family polymerases bind an incoming nucleoside triphosphate at a pre-insertion site located near the fingers subdomain before escorting it into the insertion site, whereas it has been proposed from biochemical studies that B-family polymerases bind the incoming nucleoside triphosphate directly in the insertion site at the base of the fingers. Structural studies of A-family polymerases have described a pre-insertion site for the templating base in the replication cycle of this family. Following the phosphoryl transfer reaction, the newly incorporated nucleotide moves from the insertion site to the priming site, allowing the next incoming nucleotide to bind. In some embodiments, labels can be attached to the enzyme which are sensitive to the movement of a nucleotide or nucleotide analog from the pre-insertion to the templating position, for example by labeling residues at or near the pre-insertion position on an A family polymerase. This last step, generally referred to as translocation, facilitates processive movement of a polymerase along template DNA and is therefore a critical feature of the nucleotide addition cycle of replicative polymerases.

Figure 7:
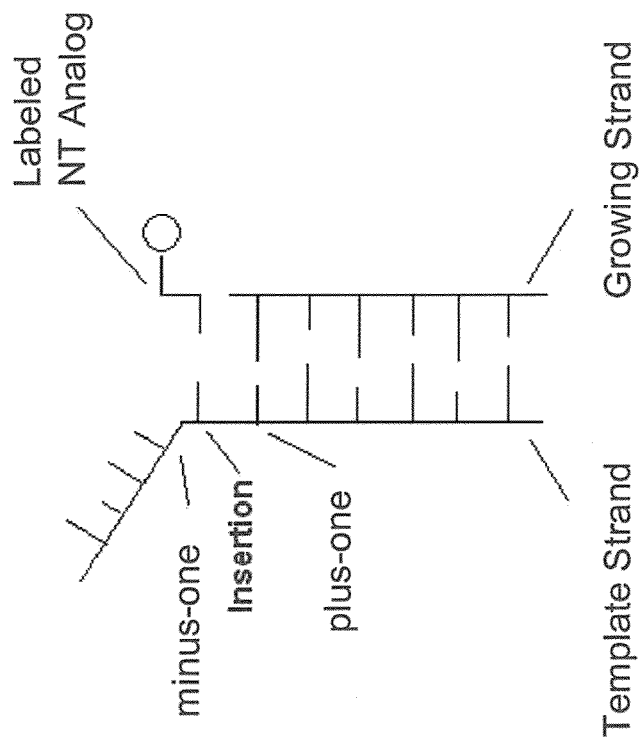
FIG. 7 shows a template nucleic acid strand hybridized to a growing strand illustrating the insertion, minus-one, and plus-one positions on the template nucleic acid strand.

In one embodiment of the invention, a signal indicative of translocation is obtained using a label which is sensitive to the check point at "minus-one" position. The minus-one position is the position on the single stranded nucleic acid template carrying the base to which the cognate base hybridizes during incorporation. The minus-one position caries the base that is next to move into the insertion position after incorporation has occurred. FIG. 7 illustrates the designation of these positions. FIG. 7 shows a nucleic acid template strand hybridized to a growing nucleotide strand. A labeled nucleotide analog is shown hybridized to the base at the insertion position on the template nucleic acid. The base in the insertion position performs a templating function with respect to the incoming nucleotide. The minus-one position on the template holds the base which will be used as the template to select the next nucleotide analog after the nucleotide analog shown in the figure is incorporated. That is, following translocation, the base in the minus-one position will occupy the insertion position, and the base in the insertion position will occupy the plus-one position.

Figure 8:
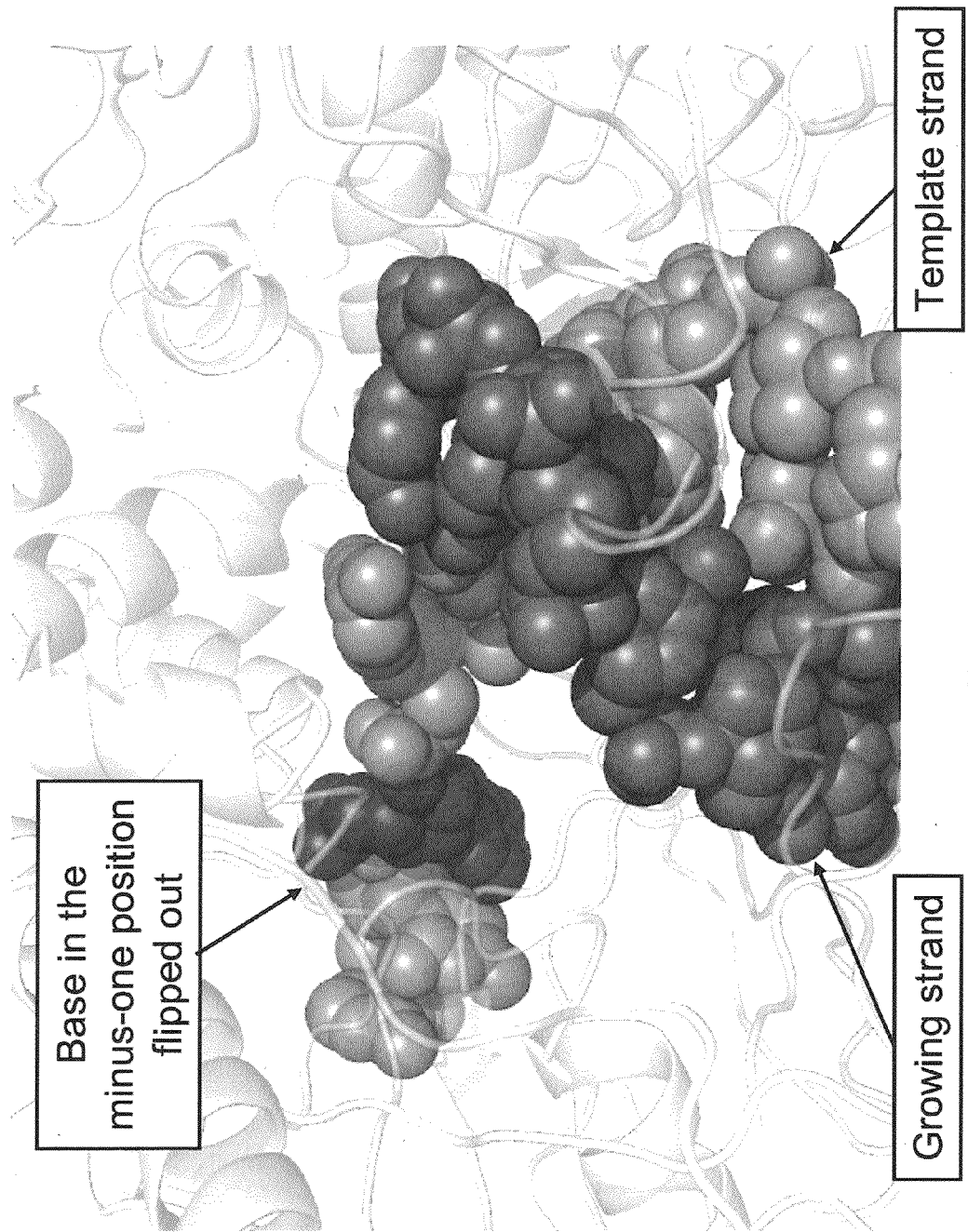
FIG. 8 shows a 3-D rendering of a portion of a phi-29 DNA polymerase in which the base at the minus-one position is flipped out from the rest of the template strand.

A common structural feature of many DNA polymerases is that the templating base at the minus-one position is flipped out. This is known to be the case, for example, for the Phi 29 DNA polymerase. FIG. 8 shows a structural model of a Phi 29 DNA polymerase and a portion of the template nucleic acid and the growing strand. FIG. 8 illustrates how the minus-one base is flipped out. After the base incorporation, DNA is translocated one step downstream. During this process, a dramatic change occurs as the flipped out base undergoes almost a 180° flipping motion from the minus-one position to the insertion position where it will act as the next templating base. This flipping motion is originally driven by the energy from the chemical reaction that occurs upon incorporation. This energy is transferred by a series of conformational change of the polymerase/DNA complex. This flipping motion is significant on the structural level; and labels at a number of positions on the enzyme can be used to sense this motion. We can use this motion as a probe to detect translocation and thus determine the occurrence of a true incorporation event.

It has been shown that signal from a 2-amino-purine residue on the DNA template strand emits a signal change when it flips from the minus-one position to the insertion position (Joyce, Biochim. Biophys. Acta, doi:10.1016/j.bbapap.2009.07.021) demonstrating the large change in the local environment in this position. For the current invention, instead of monitoring a change with a label in the template nucleic acid, one or more labels are attached to the polymerase to monitor this aspect of translocation. Labels can be attached to any position that provides a measurement of movement at the minus-one position. Suitable residues for attachment of a label include residues located around the translocation path of the flipping base. Suitable residues include, for example I93, M188, K392, V399, T421, K422, S95, Y101, M102, Q99, L123, K124, T189, A190, G191, S388, P127, L384, N387, S388, L389, Y390, and G391. Known methods of protein modification can be used to convert one or more of these residues into a labeled site. The residues can be labeled with fluorophore whose fluorescence is sensitive to environment, can be labeled with one of a donor-acceptor pair for FRET, or can be labeled with one of a donor-quencher pair. In some embodiments, one or more of the residues can be mutated to comprise a tryptophan residue.

In one aspect of the invention, a polymerase enzyme has a first label covalently attached to a first portion of the polymerase, and a second label covalently attached to a second portion of the enzyme, and the relative motion of the two labels is used as a signal of translocation, e.g. by FRET or quenching between the first and second labels. In some cases, the first label is attached to a first domain, and the second label is attached to a second domain, and relative motion between the two domains provides a signal of translocation. The first and/or second domains can be, for example, the fingers, thumb, palm, exo, or terminal protein region domains.

Opening and Closing

A significant movement between the fingers domain and the palm domain before and after the dNTP binding in the active site, which is formed by these two domains, is one signature feature of most DNA polymerases (Joyce et al., Ann. Rev. Biochem. 63, 777-822, 1994; Steitz et al., Harvey Lect. 93, 75-93, 1997). DNA polymerases such as the Phi29 DNA polymerase also have open and closed conformational states with respect to the movement of fingers and palm domain (Kamtekar, EMBO J. 25(6), 1335-43, 2006; Berman et al., EMBO J. 26(14), 3494-505, 2007). The polymerase opens its active site by moving its fingers domain away from the palm domain for accepting to the incoming dNTP. After the dNTP binding to the active site, the polymerase closes its active site by moving its fingers domain toward to the palm domain for catalyzing the dNTP hydrolysis reaction. Once the reaction is completed, the polymerase reopens its active site for releasing the pyrophosphate product and welcoming the next incoming dNTP. Real-time single-molecule DNA sequencing technology such as that described in Eid et al. Science, 323, 133-138, 2009 utilize fluorescently labeled dNTP for signaling the incorporation of this dNTP. The fluorophore resonance time, during which the incorporation of dNTP truly happens, contributes to the sequencing accuracy. To allow the fluorescent probe labeled dNTP stay on the polymerase long enough for detection and guarantee the fluorescent signal truly reflect an incorporation event of a correction dNTP, the polymerase may be modified such that the relative movement of the fingers and palm domain is altered to favor the fingers domain moving toward to the palm domain. Thus, the dynamic equilibrium between the open and closed conformations is constrained toward the closed states. The fingers and palm domain can be fluorescently labeled for monitoring the relatively movement of the two domains (Allen et al., Protein Sci. 17(3), 401-408, 2008). An additional application for monitoring the relatively movement of fingers and palm domain is to identify the non-catalytic stickness of the dNTP analysis in the enzyme active site or in the other location of the polymerase, e. g. on the surface. The fingers and palm domain move to close in most cases of dNTP analog binding to the active site.

Where the sequencing of the template involved observing the labeled nucleotide analog such as a terminal labeled analog while it is associated with the enzyme, a signal corresponding to the opening and closing of the fingers domain can be used to determine whether the a pulse that is observed corresponds to a true incorporation event.

In some cases, the signal that is indicative of whether the polymerase is in the open or closed will be the same whether a cognate or a non-cognate nucleotide or nucleotide analog is associated with the polymerase. In such cases, the signal can be useful to determine whether a pulse corresponds to a true incorporation event because of the timing of the signal and the pulse. For example, an incorporation event should include at least some portion of time in which the polymerase is in a closed conformation. Where a pulse is observed, and there is no signal indicative of a closed conformation within the time frame of the pulse, it may be suspected that the pulse does not correspond to an incorporation event.

In cases where the open-closed conformational change is sensitive to whether the nucleotide or nucleotide analog is a cognate or a non-cognate nucleotide, further information is available for correctly identifying an incorporation event. When a non-cognate nucleotide binds to the active site, the non-cognate nucleotide does not fit into the active site the way that a cognate nucleotide fits. When the enzyme moves into the closed conformation around a non-cognate nucleotide, the closure may not be as complete, resulting in a measurable difference in the signal from a closed conformation from a non-cognate as compared to a cognate nucleotide. For example, the fingers domain and palm domain may each be labeled with a member of a FRET pair such that a FRET signal is weaker when a non-cognate nucleotide binds than when a cognate nucleotide binds to the active site. (See, e.g. Allen et al., Protein Sci. 17(3), 401-408, 2008). Where the signal is measurably different between a cognate and non-cognate nucleotide, the observation of a signal indicating the biding of a cognate nucleotide can be used as an indication that a true incorporation has occurred. If a signal indicative of a cognate nucleotide or nucleotide analog is observed, concurrent with a pulse from one of the labeled nucleotides in the reaction, this provides a positive indication that incorporation has occurred. If a signal indicative of a non-cognate nucleotide is observed concurrent with at pulse from one of the labeled nucleotides in the reaction, this provides an indication that no incorporation has occurred, and that the observed event may correspond to a branching event, in which a non-cognate nucleotide is sampled by the polymerase and then released.

In some cases signal due to the opening and closing of the enzyme is obtained by providing FRET labels covalently attached to two different domains which move in relation to one another in the transition from the open to the closed conformation. For example, one FRET label can be on a residue located in the fingers domain, and the other FRET label can be located on the palm domain. In some embodiments, one FRET label is located on the fingers domain, and the other FRET label is located on the thumb domain. In some embodiments, one FRET label is located on the thumb domain and the other is located on the palm domain. In some cases, one of the FRET labels is located on the exo domain, and the other label is located on either the fingers, thumb, or palm domain. In some cases, both of the FRET labels are attached to a single domain, and the movement within the domain is sufficient to provide a signal indicative of opening and closing. For example, both of the FRET labels can be on the fingers, thumb, palm, or exo domains.

X-Ray crystal structure based studies have elucidated the relative movement of the various portions of polymerase enzymes, providing sites for the attachment of labels or pairs of labels that are sensitive to conformational changes. For example, for phi29 DNA polymerases, it has been shown that the binding of the incoming dNTP triggers a 14 degree rotation of the fingers subdomain toward the polymerase active site, corresponding to about a 0.7 nm movement of the tip of the fingers. See, for example, Berman et al. EMBO Journal, 26(14) 3494-3505. As in other polymerases, the triphosphate moiety of the incoming nucleotide acts as an electrostatic crosslink between conserved residues of the fingers and the catalytic metal ions chelated to the conserved carboxylates, thereby keeping the fingers closed. Once closed, the fingers complete the nascent base pair-binding pocket. The structure of the duplex DNA in the binary complex is distorted compared to its structure in the ternary complex. The nucleotide bases in the binary structure are substantially displaced, with the entire nucleotide at the −1 position of the template strand lifted almost 0.2 nm off the active site, whereas the positions of the phosphate backbones shift with an RMSD of less than 0.1 nm. The distortion of the duplex DNA appears to be a consequence of the position of the templating nucleotide. When the fingers are closed, the nascent base pair binding pocket holds the templating nucleotide in position and the upstream bases of the template strand stack accordingly. However, in the binary complex, where the fingers are opened, the residues completing the nascent base pair binding pocket are too far away to stabilize the nucleotide in the templating position. This results in the displacement of the templating nucleotide by about 0.15 nm upstream from its position in the ternary complex; the stacking of the upstream nucleotides follows, slightly distorting the duplex. Similar systematic shifts are observed in comparing the binary and ternary complexes of the A-family polymerases and X-family polymerases.

The opening of the fingers that occurs in the transition from the ternary complex to the binary complex is accompanied by several mechanistically significant changes. When the fingers open, the side chain of Y390 from a conserved sequence motif moves into the insertion site, such that the newly incorporated nucleotide can no longer reside there.

These characterized shifts in the relative positions of the domains of the polymerases provide for choosing the positions for attaching labels to the polymerase enzymes to monitor conformational changes. One of skill in the art would be able to select and readily test the efficacy of attachment to positions which show significant movement at specific enzymatic steps. This observation is consistent with biochemical data suggesting that Y390 interacts either directly or indirectly with the incoming dNTP. If no nucleotide occupies the insertion site, the steric gate residue (Y254) can flip to its most favorable rotamer. This rotamer places the phenolic ring of the steric gate residue directly in the insertion site, stacking on the conserved tyrosine at the base of the fingers (Y390), one of the most energetically stable tyrosine-tyrosine interactions. The positions of both of these tyrosine residues in the insertion site preclude the primer terminus from binding at the insertion site while the fingers are opened. Therefore, the primer terminus must move to the priming site, resulting in translocation of the DNA by one nucleotide. The rotation of Y390 breaks its hydrogen bond with Y226, a residue in the conserved B-family I/YxGG/A sequence motif that has been proposed to be involved in template binding at the active site and in protein priming. In the structures of these complexes, this motif stabilizes the nucleotides in the −1 and −2 positions of the template strand by van der Waals and hydrogen-bonding interactions, as predicted by mutagenesis studies in B-family Polymerases. The residues, regions, and domains described herein which provide movement due to conformational changes can be labeled and used in accordance with this invention to sequence nucleic acid templates using such labeled polymerases.

Recombinant enzymes modified for improved single molecule sequencing performance can be used with these methods. Suitable enzymes are described, for example in U.S. patent Ser. No. 11/645,223 filed Dec. 21, 2006, U.S. patent Ser. No. 11/977,160 filed Oct. 22, 2007, U.S. patent Ser. No. 12/384,112 filed Mar. 30, 2009, and U.S. patent Ser. No. 12/384,110 filed Mar. 30, 2009, the contents of which are incorporated by reference herein in their entirety for all purposes Downstream Template Binding Regions In some cases, residues associated with the binding of the downstream template can be used as an indication of conformational change. As expected for a processive replicative polymerase, phi29 DNAP is believed to interact with ssDNA in a sequence nonspecific manner. In the complexes containing ssDNA, residues in the downstream template tunnel interact with the two nucleotides that lie immediately downstream (+1 and +2) of the templating nucleotide (0). The base of the +1 nucleotide on the template strand is unstacked from the bases of adjacent nucleotides of the single-stranded 5 prime template overhang. The base of this unstacked nucleotide fits into a pocket formed by residues V399 and K422 (TPR2 subdomain) and I93 (exonuclease domain) and completed by the nucleotide 5 prime to the unstacked nucleotide, whereas the sugar stacks on the side chain of Y101. The downstream template tunnel does not pack tightly around the unstacked pyrimidine base and is large enough to accommodate a purine base, suggesting that during processive synthesis, the size of the downstream template tunnel may remain constant. The +2 nucleotide sits on a hydrophobic surface formed by exonuclease residues M102, I93, and M188. The large number of hydrophobic interactions with the bases in the downstream template tunnel compensates for the energy lost by unstacking the +1 nucleotide.

Several hydrophilic residues at the edges of the downstream template tunnel stabilize the polar groups of the nucleotides. Residues Y101, T189, S192, K392, and N396 interact with the backbone through water-mediated and direct hydrogen bonds. The +2 nucleotide interacts through water-mediated hydrogen bonds with D104 and N91. Finally, within the downstream template tunnel, the functional group at the C6 position of a +1 purine interacts with the phosphate of the +2 nucleotide; no interaction between this phosphate and a +1 pyrimidine is observed From amino acid sequence comparisons as well as crystal structure analyses, the DNA polymerases have been divided into at least five different families.

While these polymerases have significant differences in their detailed structure, polymerases generally share common overall architectural features. They have a shape that can be compared with that of a right hand and have been described as consisting of "thumb," "palm," and "fingers" domains. A function of the palm domain is catalysis of the phosphoryl transfer reaction whereas that of the fingers domain includes important interactions with the incoming nucleoside triphosphate as well as the template base to which it is paired. The thumb on the other hand may play a role in positioning the duplex DNA and in processivity and translocation. Although the palm domain appears to be somewhat homologous among the pol I, pol a, and RT families, the fingers and thumb domains can be quite different among the families.

Although the structures of the thumb domains are not homologous, they do exhibit analogous features that consist of largely parallel or anti-parallel a-helices and in each case at least one a-helix seems to be making important interactions across the minor groove of the primer-template product. In the case of the pol I family, loops at the top of the thumb also make important and conserved interactions with the DNA backbone. As these enzymes have known and common movements of the thumb domain, labels attached to the thumb domain of these polymerases can be used to indicate enzyme conformation The same can be seen for the fingers domains of the polymerase enzymes. Although the fingers domains of the various families may not be homologous, there are some striking structural analogies among the families as with the thumbs. For example, in the pol I, pol a, and pal b families, an a-helix in the fingers domain is positioned at the blunt end of the primer-template; it contains side chains that are conserved within the families (the B motif) and provides important orienting interactions with the incoming deoxynucleoside triphosphate. In the case of the reverse transcriptase family, however, some of these functions are performed by an antiparallel b-ribbon, which lies in a similar position. Labels on these domains can also be used in accordance with the invention to provide conformational information to provide for more accurate nucleic acid sequencing.

Aspects of the present invention involve the measurement of changes in conformation of a polymerase enzyme at the same time that the addition of specific nucleotides or nucleotide analogs to the growing strand is being optically monitored. The changes in enzyme conformation can provide information which can significantly enhance the accuracy of a sequence determination. The detection of changes in enzyme conformation can be done in any suitable manner. The detection must generally be sensitive enough to monitor a single molecule while the polymerase reaction is taking place. In some cases, the detection is carried out optically. Fluorescence or luminescence detection provides for detection at this level of sensitivity.

As the enzyme undergoes polymerization, it undergoes a series of movements. As it undergoes these movements, it can be seen as reproducibly adopting a series of conformations. In the different conformations, various portions of the enzyme move relative to one another. In some cases, the conformational of the enzyme can be characterized as going from one discrete conformational state to another. These states can be, for example an open conformation and a closed conformation. For the method and systems of the inventions, however, it is not required that there exist distinct states in order for a measurement of conformational change to occur. What is required is that the signal that is sensitive to enzyme conformation changes reproducibly during the polymerase reaction. For example, as one portion of the enzyme moves relative to another portion of the enzyme during the polymerase reaction, one portion of the enzyme may sweep past another portion of the enzyme during one or more steps. Where this occurs, for instance, labels attached to the two portions of the enzyme that are moving relative to each other may exhibit a strongly increased FRET signal as they are moved close to one another and then move apart. Thus, in some cases of the invention there are two, three, four or more discrete states which can be identified that result in different signal levels. In some cases, the signal will result from transient signals generated as the enzyme moves, for example, from one state to another.

Label Sensitive to Local Environment

In some cases, a fluorescent dye that is sensitive to changes in its local environment can be used to detect conformational changes. Fluorescent dyes are known, for example in which the torsional motion of double bonds in its excited state can bring the dye back to its electronic ground state without photon emission. Constraints of the torsional motion hinder the nonradiative decay pathway, giving a higher fluorescence quantum yield. In other cases the fluorescence quantum yield of a dye can have a strong solvent viscosity dependence. Fluorescent dyes can also have emissions which are highly sensitive to the polarity or H-bonding characteristics of its immediate environment. In some cases, the label can be sensitive to the proximity of specific amino acid residues in the vicinity of the label. For example, the label can be sensitive to the presence of aromatic amino acids, charged amino acids, basic amino acids, acidic amino acids in its vicinity. As the enzyme undergoes conformational changes, such residues will move closer to and then further away from the label, providing a measure of the conformation of the enzyme. Such amino acids can interact with the electronic states of the extended molecular oribitals the label, e.g. a fluorescent dye. Alternatively, the amino acid could interact directly with one or more functional groups on the label, for example a H bonding, charge transfer, or acid-base interaction. These properties can make the appropriate fluorescent dye a probe for detecting subtle conformational alterations within an intact protein or protein complex.

For example, a dye such as Cy3 dye attached can provide a measurement of polymerase enzyme conformational change at the level of a single molecule. See Luo et al. PNAS, 104(31) 12610-12615, 2007. Fluorescent dyes sensitive to the local environment in a protein include, for example, Acrylodan, NBD, NBDE, Fluorescein, Pyrene, or the styryl and napthyl dyes JPW4039, JPW4042, and JPW4045 (U.S. Patent Application 20080166747).

Interactions between the label and nucleic acids associated with the polymerase can also contribute to the changes in local environment indicative of conformational changes. For example, the label attached to the polymerase may interact with residues on the template, primer or growing strand. These interactions can provide changes to the local environment of the dye which depend on changes in conformation.

Fluorophores may include derivatives of cyanine (e.g. thiazole orange and oxazole yellow), indole, bisbenzimide, phenanthridine, pyrene, naphthalene, pyridyloxazole, dapoxyl, and acridine. Other fluorophores may include, but are not limited to, acridone and quinacridone derivatives (Amersham Biosciences, WO/20003099432 and WO/2003099424), 2,3 diazabicyclo[2.2.2]-oct-gene derivatives, Nile Red, Dansyl, and merocyanine derivatives (e.g. Toutchkine et al., 2003, J. Am. Chem. Soc., 125:4132-4145).

Fluorophores may also include the fluorophores which are attached to the enzyme subsequent to reaction with, for example, the reactive derivatives: 1-pyrenebutanoic acid, succinimidyl ester; 2-dimethylaminonaphthalene-6-sulfonyl chloride; 2-(4'-(iodoacetamido)anilino)naphthalene-6-sulfonic acid, sodium salt (IAANS); 2-(4'-maleimidylanilino) naphthalene-6-sulfonic acid, sodium salt (MIANS); 6-acryloyl-2-dimethylaminonaphthalene (acrylodan); 6-bromoacetyl-2-dimethyl-aminonaphthalene (badan); 6-((5-dimethylaminonaphthalene-1-sulfonyl)amino)-hexanoic acid, succinimidyl ester (dansyl-X, SE); 1-(2-maleimidylethyl)-4-(5-(4-methoxyphenyl)oxazol-2-yl)pyridinium methanesulfonate (PyMPO maleimide); Dapoxyl® 3-sulfonamidopropionic acid, succinimidyl ester; Bodipy fluorophores (e.g. 576, R6G, TMR, TR); and reactive forms of SYBR Green I and Picogreen (e.g. SYBR, S-21500, S-21501, S-21502) (Molecular Probes, Eugene, Oreg.). Willets, et al., 2004, J. Phys. Chem. B, 108(29):10465-10473, provides further embodiments of environmentally sensitive fluorophores suitable for use in the invention. Environmentally sensitive dyes provide an advantage of signaling conformational change using only one label attached to the polymerase enzyme.

In some cases, the interaction between two dyes, both attached to the polymerase, is used to indicate a conformational change. The use of two dyes, while more complicated in terms of preparation than the use of one dye, can provide higher sensitivity to small movements of the polymerase. The interaction between the two dyes can result in either the enhancement of fluorescence, or in the quenching of fluorescence as the dyes are moved into proximity. Enhancement of fluorescence can be produced, for example, by using fluorescence resonance energy transfer (FRET) between a donor and an acceptor dye.

Fluorescence resonance energy transfer, also termed Förster resonance energy transfer and abbreviated as FRET, generally comprises an energy transfer that occurs between two chromophores, namely, an energy donor and an energy acceptor as a result of absorption of excitation light by the energy donor. The energy transfer generally occurs through a coupled dipole-dipole interaction and a nonradiative transfer from donor to acceptor, without generation of an intermediate photon. The efficiency of energy transfer are strongly dependent on the separation distance between the donor and acceptor, such as varying by an inverse sixth power law, wherein the amount of energy transferred drops of at the $6^{th}$ power of the distance between the donor and acceptor. Accordingly, most FRET, for practical purposes, may be limited to a separation distance of less than about ten nanometers. Also, the efficiency of energy transfer is generally dependent on the spectral overlap of donor emission and acceptor absorption. After transfer of the energy from the donor to the acceptor, the acceptor can emit the energy transferred to it, generating a fluorescent signal with its characteristic fluorescent emission spectrum.

A FRET member or a member of a FRET pair generally comprises an energy donor or an energy acceptor of a donor-acceptor pair capable of FRET when in close proximity and with exposure to excitation light of a suitable wavelength. Accordingly, members of a FRET pair generally are or include a donor having an emission spectrum that overlaps the absorption spectrum of the acceptor In general, a fluorescent acceptor moiety should exhibit a good quantum yield and a large extinction coefficient; should be resistant to collisional quenching and bleaching; and should be easily conjugated to a variety of compositions and probe compositions by methods known to those having ordinary skill in the art. Suitable fluorophores include, without limitation, fluorescein, rhodamine, FITCs (e.g., fluorescein-5-isothiocyanate), 5-FAM, 6-FAM, 5,6-FAM, 7-hydroxycoumarin-3-carboxamide, 6-chloro-7-hydroxycoumarin-3-carboxamide, dichlorotriazinylaminofluorescein, tetramethylrhodamine-5-isothiocyanate, tetramethylrhodamine-6-isothiocyanate, succinimidyl ester of 5-carboxyfluorescein, succinimidyl ester of 6-carboxyfluorescein, 5-carboxytetramethylrhodamine, 6-carboxymethylrhodamine, and 7-amino-4-methylcoumarin-3-acetic acid. Other suitable fluorophores include the Cy family of fluorophores (Cy 3, Cy3B, Cy3.5, Cy5; available from Amersham Biosciences, Piscataway, N.J.); the Alexa Fluor family (available from Molecular Probes, Eugene, Oreg.); the BODIPY family (available from Molecular Probes, Eugene, Oreg.); carbopyronins; squarines; cyanine/indocyanines; benzopyrylium heterocyles; and amide-bridged benzopyryliums.

The donor-acceptor pair may be described as a FRET pair. Exemplary FRET pairs may include fluorescein/rhodamine, Cy3/Cy5, lanthanide/phycobiliprotein, lanthanide/Cy5, cyan fluorescent protein (CFP)/yellow fluorescent protein (YFP), fluorescein/tetramethylrhodamine, 5-(2'-aminoethyl)-aminoapthalene-1-sulfonic acid (EDANS)/fluorescein and EDANS/DABCYL among others. Donor and acceptor molecules suitable for FRET are well known in the art (see R. P. Haugland, Handbook of Fluorescent Probes and Research Chemicals, 6th ed.; Molecular Probes, Oregon, the teachings of which are incorporated herein by reference).

In some embodiments, the donor fluorophore comprises Atto532 where the donor fluorophore comprises PB570 or Alexa568, providing a green FRET system for use with labeled nucleotides having a gap in their excitation spectra in this wavelength range, which uses, for example Alexa555, and Alexa594 or Biotium 052-125. In some cases, a red FRET system is used, for example using a 532 nm laser not excite analogs Alexa555-dT6P, PB570/Alexa568-dG6P, and Alexa594/Biotium052-125-dC6P; and a 643 nm laser to excite PB692-dA6P and a PB650 FRET donor, which transfers energy to the FRET acceptor A647.

Fluorescent proteins and mutants can also be used as fluorescent acceptor moieties. Examples include firefly, bacterial, or click beetle luciferases, aequorins, and other photoproteins (for example as described in U.S. Pat. No. 5,221,623, and U.S. Pat. No. 5,683,888) GFP and GFP mutants can be useful. See, e.g. Green Fluorescent Proteins, Chapter 2, pages 19 to 47, edited by Sullivan and Kay, Academic Press; U.S. Pat. No. 5,625,048, and U.S. Pat. No. 5,777,079).

Quenching

In some cases, the enzyme conformational change signal uses the quenching between a fluorescent label and a quencher, a donor-acceptor pair. As with FRET, quenching provided a signal which can be sensitive to changes in distance on the order of 0.1 nm to 10 nm. The donor-acceptor pair can be attached in any of the positions described herein with respect to FRET pairs. In some cases, the quenching may be part of a FRET process. FRET detection allows for the observation from the acceptor fluorophore, providing a signal which becomes higher in intensity as the donor and acceptor get closer together. Quenching generally provides a system in which the signal of the donor is observed, and the intensity of the signal becomes lower in intensity as the donor and quencher get closer together. Thus, FRET and quenching can provide a different type of measurement for a given conformational change.

Any suitable quencher can be used. In some cases, a quenching molecule is a weakly fluorescent dye.

Suitable quenchers include dark quenchers, molecules which provide quenching of a donor fluorophore, but have little or no fluorescence of their own. Examples of quenchers include, but are not limited to DABCYL (4-(4'-dimethylaminophenylazo)benzoic acid) succinimidyl ester, diarylrhodamine carboxylic acid, succinimidyl ester (QSY-7), and 4',5'-dinitrofluorescein carboxylic acid, succinimidyl ester (QSY-33) (all available from Molecular Probes), IRDye QC-1 from Li-Cor Biosciences, and quenchers Redmond Red™, Yakima Yellow™, and Eclipse™ available from Epoch or Glen Biosciences. Suitable quenchers include black hole quenchers such as BHQ1, BHQ3, and BHQ2 and other quenchers as described on the Biosearch Technologies website.

Non-Optical Detection

The changes in conformation are generally determined optically, but in some cases other methods of detection such as electronic or electrochemical detection can be used. For example, charge transport through can be exquisitely sensitive to pi-stacking and has yielded sensitive assays in mutational analysis based upon the detection of base-stacking perturbations such as mismatches. In electrochemistry experiments using DNA films, redox-active intercalators, such as daunomycin, that are covalently crosslinked or non-covalently bound to the modified surface can be efficiently reduced. However, the presence of a mis-paired base between the electrode and the site of intercalation switches off the electrochemical response. By coupling the reduction of the intercalator to an electrocatalytic cycle, all single base mismatches, including thermodynamically stable GT and GA mismatches as well as many DNA base lesions can be discriminated. Spectroscopic and biochemical studies of oxidative damage at a distance have also revealed sensitivity to disruptions in the pi-stack, which are present with mismatches or base-flipping enzymes. Using such electronic or electrochemical detection can be used to probe protein binding in order to provide electrochemical detection of DNA or RNA base-stacking perturbations. Electrochemical methods of monitoring proteins can be used to monitor protein conformational changes, and can be coupled with the optical measurement of labeled base association with polymerase enzymes to improve the accuracy of sequencing. Suitable electrochemical systems are described, for example in Boon et al. Nature Biochemistry 20, 282-286, 2007.

Terms

The term "nucleic acid" or "polynucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. A particular nucleic acid sequence of this invention can encompasses complementary sequences, in addition to the sequence explicitly indicated.

The term "nucleotide" can be used to refer either to the monomer reactant that is present prior to addition to the growing strand, e.g. the NTP or dNTP, or can be used to refer to the monomeric unit that is part of the growing nucleic acid. It is understood that when the nucleotide (e.g. dNTP) is incorporated into the growing strand that a portion of the nucleotide is cleaved upon incorporation (e.g. the pyrophosphate). Whether the term is used in the sense of the reactant or the monomeric unit will be clear to one of skill in the art from the context. For example, it is understood that the nucleotide can have a label on the portion of the nucleotide that is cleaved upon incorporation. Thus when it is stated, for example, that a labeled nucleotide is incorporated, it is to be understood that the term nucleotide is referring to the reagent, e.g. the dNTP, and if the dNTP is labeled on the portion that is cleaved, the portion of the nucleotide that is incorporated would not bear a label. The same is true for the term nucleotide analog. That is, where a nucleotide analog is incorporated into a growing nucleic acid, if the nucleotide analog is labeled on the portion of the nucleotide analog that is cleaved, then the label will be released and will not be incorporated into growing strand.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Numbering of a given amino acid or nucleotide polymer "corresponds to numbering of" or is "relative to" a selected amino acid polymer or nucleic acid when the position of any given polymer component (amino acid residue, incorporated nucleotide, etc.) is designated by reference to the same residue position in the selected amino acid or nucleotide, rather than by the actual position of the component in the given polymer. Correspondence of positions is typically determined by aligning the relevant amino acid or polynucleotide sequences.

The term "recombinant" indicates that the material (e.g., a nucleic acid or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is, e.g., a polypeptide or protein which is produced by expression of a recombinant nucleic acid.

A "Φ29-type DNA polymerase" (or "phi29-type DNA polymerase") is a DNA polymerase from the Φ29 phage or from one of the related phages that, like Φ29, contain a terminal protein used in the initiation of DNA replication. Φ29-type DNA polymerases are homologous to the Φ29 DNA polymerase; examples include the B103, GA-1, PZA, Φ15, BS32, M2Y, Nf, G1, Cp-1, PRD1, PZE, SF5, Cp-5, Cp-7, PR4, PR5, PR722, and L17 DNA polymerases, as well as chimeras thereof. A modified recombinant Φ29-type DNA polymerase includes one or more mutations relative to naturally-occurring wild-type Φ29-type DNA polymerases, for example, one or more mutations that increase closed complex stability, decrease branching fraction, and/or slow a catalytic step relative to a corresponding wild-type polymerase, and may include additional alterations or modifications over wild-type Φ29-type DNA polymerases, such as deletions, insertions, and/or fusions of additional peptide or protein sequences (e.g., for immobilizing the polymerase on a surface or otherwise tagging the polymerase enzyme).

Polymerase Enzymes

Polymerase enzymes having labels indicative of polymer conformation can include polymerases mutated to have desirable properties for sequencing. For example, suitable enzymes include those taught in, e.g., WO 2007/076057 POLYMERASES FOR NUCLEOTIDE ANALOGUE INCORPORATION by Hanzel et al., WO 2008/051530 POLYMERASE ENZYMES AND REAGENTS FOR ENHANCED NUCLEIC ACID SEQUENCING by Rank et al., and U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES." The modified polymerases may have modified properties such as (e.g., decreased branch fraction formation, improved specificity, improved processivity, altered rates, improved retention time, improved stability of the closed complex, etc.).

In addition, the polymerases can be further modified for application-specific reasons, such as to increase photostability, e.g., as taught in U.S. patent application Ser. No. 12/384, 110 filed Mar. 30, 2009, by Keith Bjornson et al. entitled "Enzymes Resistant to Photodamage," to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

DNA Polymerases

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clarkson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, a M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied. Science, Sigma Aldrich and many others. The Klenow fragment of DNA Polymerase I is available in both recombinant and protease digested versions, from, e.g., Ambion, Chimera, eEnzyme LLC, GE Health Care, Invitrogen, New England Biolabs, Promega, Roche Applied Science, Sigma Aldrich and many others. Φ29 DNA polymerase is available from e.g., Epicentre. PolyA polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, Φ29 related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. No. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287.

RNA Polymerases

In some embodiments, the polymerase enzyme that is used for sequencing is an RNA polymerase. Any suitable RNA polymerase can be used including RNA polymerases from bacteria, eukaryotes, viruses, or archea. Suitable RNA polymerases include RNA Pol I, RNA Pol II, RNA Pol III, RNA Pol IV, RNA Pol V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors. There are many proteins that can bind to RNAP and modify its behavior. For instance, GreA and GreB from *E. coli* and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e. they help RNAP choose whether or not to express certain genes. RNA dependent RNA polymerases (RNA replicases) may also be used including viral RNA polymerases: e.g. polioviral 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or systems of the invention include RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Reaction Conditions

Recombinant polymerases of the invention are optionally modified in a manner in which the relative rates of steps of the polymerization reaction are changed, for example, such that the polymerase is capable of showing two slow step characteristics. The reaction conditions can also affect reaction rates. Reaction conditions can thus be manipulated, for example, to further slow a step or steps which are already slowed in a modified polymerase, or to slow an additional step, such that the resulting polymerase system exhibits two slow step behavior.

The polymerase reaction conditions include, e.g., the type and concentration of buffer, the pH of the reaction, the temperature, the type and concentration of salts, the presence of particular additives which influence the kinetics of the enzyme, and the type, concentration, and relative amounts of various cofactors, including metal cofactors. Manipulation of reaction conditions to achieve or enhance two slow step behavior of polymerases is described in detail in U.S. patent application Ser. No. 12/414,191 filed Mar. 30, 2009, and entitled "Two slow-step polymerase enzyme systems and methods."

Enzymatic reactions are often run in the presence of a buffer, which is used, in part, to control the pH of the reaction mixture. The type of buffer can in some cases influence the kinetics of the polymerase reaction in a way that can lead to two slow-step kinetics. For example, in some cases, use of TRIS as buffer is useful for obtaining a two slow-step reaction. Suitable buffers include, for example, TAPS (3-{[tris (hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl) methylglycine), HEPES 4-2-hydroxyethyl-1-piperazineethanesulfonic acid), TES (2-{[tris (hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction, and can be used as one of the polymerase reaction conditions to obtain a reaction exhibiting two slow-step kinetics. The pH can be adjusted to a value that produces a two slow-step reaction mechanism. The pH is generally between about 6 and about 9. In some cases, the pH is between about 6.5 and about 8.0. In some cases, the pH is between about 6.5 and 7.5. In some cases, the pH is about 6.5, 6.6, 6.7, 6.8, 6.9, 7.0, 7.1, 7.2, 7.3, 7.4, or 7.5.

The temperature of the reaction can be adjusted in order to obtain a reaction exhibiting two slow-step kinetics. The reaction temperature may depend upon the type of polymerase which is employed. Temperatures between 15° C. and 90° C., between 20° C. and 50° C., between 20° C. and 40° C., or between 20° C. and 30° C. can be used.

In some cases, additives can be added to the reaction mixture that will influence the kinetics of the polymerase reaction in a manner that can lead to two slow-step kinetics. In some cases, the additives can interact with the active site of the enzyme, acting for example as competitive inhibitors. In some cases, additives can interact with portions of the enzyme away from the active site in a manner that will influence the kinetics of the reaction so as to produce a reaction exhibiting two slow steps. Additives that can influence the kinetics include, for example, competitive but otherwise unreactive substrates or inhibitors in analytical reactions to modulate the rate of reaction as described in copending U.S. Utility patent application Ser. No. 12/370,472, the full disclosure of which is incorporated herein by reference in its entirety for all purposes.

As another example, an isotope such as deuterium can be added to influence the rate of one or more step in the polymerase reaction. In some cases, deuterium can be used to slow one or more steps in the polymerase reaction due to the deuterium isotope effect. By altering the kinetics of steps of the polymerase reaction, in some instances two slow step kinetics, as described herein, can be achieved. The deuterium isotope effect can be used, for example, to control the rate of incorporation of nucleotide, e.g., by slowing the incorporation rate. Isotopes other than deuterium can also be employed, for example, isotopes of carbon (e.g. $^{13}C$), nitrogen, oxygen, sulfur, or phosphorous.

As yet another example, additives that can be used to control the kinetics of the polymerase reaction include the addition of organic solvents. The solvent additives are generally water soluble organic solvents. The solvents need not be soluble at all concentrations, but are generally soluble at the amounts used to control the kinetics of the polymerase reaction. While not being bound by theory, it is believed that the solvents can influence the three dimensional conformation of the polymerase enzyme which can affect the rates of the various steps in the polymerase reaction. For example, the solvents can affect steps involving conformational changes such as the isomerization steps. Added solvents can also affect, and in some cases slow, the translocation step. In some cases, the solvents act by influencing hydrogen bonding interactions.

The water miscible organic solvents that can be used to control the rates of one or more steps of the polymerase reaction in single molecule sequencing include, e.g., alcohols, amines, amides, nitriles, sulfoxides, ethers, and esters and small molecules having more than one of these functional groups. Exemplary solvents include alcohols such as methanol, ethanol, propanol, isopropanol, glycerol, and small alcohols. The alcohols can have one, two, three, or more alcohol groups. Exemplary solvents also include small molecule ethers such as tetrahydrofuran (THF) and dioxane, dimethylacetamide (DMA), dimethylsulfoxide (DMSO), dimethylformamide (DMF), and acetonitrile.

The water miscible organic solvent can be present in any amount sufficient to control the kinetics of the polymerase reaction. The solvents are generally added in an amount less than 40% of the solvent weight by weight or volume by volume. In some embodiments the solvents are added between about 0.1% and 30%, between about 1% and about 20%, between about 2% and about 15%, and between about 5% and 12%. The effective amount for controlling the kinetics can be determined by the methods described herein and those known in the art.

One aspect of controlling the polymerase reaction conditions relates to the selection of the type, level, and relative amounts of cofactors. For example, during the course of the polymerase reaction, divalent metal co-factors, such as magnesium or manganese, will interact with the enzyme-substrate complex, playing a structural role in the definition of the active site. For a discussion of metal co-factor interaction in polymerase reactions, see, e.g., Arndt, et al., Biochemistry (2001) 40:5368-5375. Suitable conditions include those described in U.S. patent application Ser. No. 12/384,112 filed Mar. 30, 2009.

Structure-Based Design of Recombinant Polymerases

Structural data for a polymerase can be used to conveniently identify amino acid residues as candidates for mutagenesis to create recombinant polymerases, for example, having modified domain interfaces to improve complex stability and/or modified active site regions that reduce branching and/or reaction rates. For example, analysis of the three-dimensional structure of a polymerase such as Φ29 can identify residues that are in the active polymerization site of the enzyme, residues that form part of the nucleotide analog binding pocket, and/or amino acids at an interface between domains.

The three-dimensional structures of a large number of DNA polymerases have been determined by x-ray, crystallography and nuclear magnetic resonance (NMR) spectroscopy, including the structures of polymerases with bound templates, nucleotides, and/or nucleotide analogs. Many such structures are freely available for download from the Protein Data Bank, at (www(dot)rcsb(dot)org/pdb. Structures, along with domain and homology information, are also freely available for search and download from the National Center for Biotechnology Information's Molecular Modeling DataBase, at www(dot)ncbi(dot)nlm(dot)nih(dot)gov/Structure/MMDB/mmdb(dot)shtml. The structures of Φ29 polymerase, Φ29 polymerase complexed with terminal protein, and Φ29 polymerase complexed with primer-template DNA in the presence and absence of a nucleoside triphosphate are available; see Kamtekar et al. (2004) "Insights into strand displacement and processivity from the crystal structure of the protein-primed DNA polymerase of bacteriophage Φ29" Mol. Cell 16(4): 609-618), see Kamtekar et al. (2006) "The phi29 DNA polymerase:protein-primer structure suggests a model for the initiation to elongation transition" EMBO J. 25(6):1335-43, and Berman et al. (2007) "Structures of phi29 DNA polymerase complexed with substrate: The mechanism of translocation in B-family polymerases" EMBO J. 26:3494-3505, respectively. The structures of additional polymerases or complexes can be modeled, for example, based on homology of the polymerases with polymerases whose structures have already been determined. Alternatively, the structure of a given polymerase (e.g., a wild-type or modified polymerase), optionally complexed with a DNA (e.g., template and/or primer) and/or nucleotide analog, or the like, can be determined.

Techniques for crystal structure determination are well known. See, for example, McPherson (1999) Crystallization of Biological Macromolecules Cold Spring Harbor Laboratory; Introduction to Macromolecular Crystallography Wiley-Liss; McRee and David (1999), and Practical Protein Crystallography, Second Edition Academic Press; Drenth (1999). In addition, a variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" Methods in Enzymology 276: 307-326), the CCP4 package (Collaborative Computational Project (1994) "The CCP4 suite: programs for protein crystallography" Acta Crystallogr D 50:760-763), SOLVE and RESOLVE (Terwilliger and Berendzen (1999) Acta Crystallogr D 55 (Pt 4):849-861), SHELXS and SHELXD (Schneider and Sheldrick (2002) "Substructure solution with SHELXD" Acta Crystallogr D Biol Crystallogr 58:1772-1779), Refmac5 (Murshudov et al. (1997) "Refinement of Macromolecular Structures by the Maximum-Likelihood Method" Acta Crystallogr D 53:240-255), PRODRG (van Aalten et al. (1996) "PRODRG, a program for generating molecular topologies and unique molecular descriptors from coordinates of small molecules" J Comput Aided Mol Des 10:255-262), and O (Jones et al. (1991) "Improved methods for building protein models in electron density maps and the location of errors in these models" Acta Crystallogr A 47 (Pt 2):110-119).

Techniques for structure determination by NMR spectroscopy are similarly well described in the literature. See, e.g., Cavanagh et al. (1995) Protein NMR Spectroscopy: Principles and Practice, Academic Press; Levitt (2001) Spin Dynamics: Basics of Nuclear Magnetic Resonance, John Wiley & Sons; Evans (1995) Biomolecular NMR Spectroscopy, Oxford University Press; Wüthrich (1986) NMR of Proteins and Nucleic Acids (Baker Lecture Series), Kurt Wiley-Interscience; Neuhaus and Williamson (2000). The structure of a polymerase, or polymerase bound to a DNA or with a given nucleotide analog incorporated into the active site can, as noted, be directly determined, e.g., by x-ray crystallography or NMR spectroscopy, or the structure can be modeled based on the structure of the polymerase and/or a structure of a polymerase with a natural nucleotide bound. The active site or other relevant domain of the polymerase can be identified, for example, by homology with other polymerases, examination of polymerase-template or polymerase-nucleotide co-complexes, biochemical analysis of mutant polymerases, and/or the like. The position of a nucleotide analog (as opposed to an available nucleotide structure) in the active site can be modeled, for example, by projecting the location of non-natural features of the analog (e.g., additional phosphate or phosphonate groups in the phosphorus containing chain linked to the nucleotide, e.g., tetra, penta or hexa phosphate groups, detectable labeling groups, e.g., fluorescent dyes, or the like) based on the previously determined location of another nucleotide or nucleotide analog in the active site.

Such modeling of the nucleotide analog or template (or both) in the active site can involve simple visual inspection of a model of the polymerase, for example, using molecular graphics software such as the PyMOL viewer (open source, freely available on the World Wide Web at www(dot)pymol(dot)org), Insight II, or Discovery Studio 2.1 (commercially available from Accelrys at (www(dot)accelrys(dot)com/products/discovery-studio). Alternatively, modeling of the active site complex of the polymerase or a putative mutant polymerase, for example, can involve computer-assisted docking, molecular dynamics, free energy minimization, and/or like calculations. Such modeling techniques have been well described in the literature; see, e.g., Babine and Abdel-Meguid (eds.) (2004) *Protein Crystallography in Drug Design*, Wiley-VCH, Weinheim; Lyne (2002) "Structure-based virtual screening: An overview" Drug Discov. Today 7:1047-1055; Molecular Modeling for Beginners, at (www(dot)usm(dot)maine(dot)edu/~rhodes/SPVTut/index(dot)html; and Methods for Protein Simulations and Drug Design at (www(dot)dddc(dot)ac(dot)cn/embo04; and references therein. Software to facilitate such modeling is widely available, for example, the CHARMm simulation package, available academically from Harvard University or commercially from Accelrys (at www(dot)accelrys(dot)com), the Discover simulation package (included in Insight II, supra), and Dynama (available at (www(dot)cs(dot)gsu(dot)edu/~cscrwh/progs/progs(dot)html). See also an extensive list of modeling software at (www(dot)netsci(dot)org/Resources/Software/Modeling/MMMD/top(dot)html.

Visual inspection and/or computational analysis of a polymerase model, including optional comparison of models of the polymerase in different states, can identify relevant features of the polymerase, including, for example, residues that can be mutated to stabilize the closed complex of the polymerase, to decrease branching, and to alter rate constants. Such residues can include, for example, amino acid residues of domains that are in close proximity to one another (to stabilize inter-domain interactions), residues in an active site or binding pocket that interact with a nucleotide or analog, DNA, or product, residues that modulate how large a binding pocket is relative to the analog, etc.

Determining Kinetic Parameters

The polymerases of the invention can be screened or otherwise tested to determine whether the polymerase displays a modified activity for or with a nucleotide analog or template as compared to a parental DNA polymerase (e.g., a corresponding wild-type or available mutant polymerase from which the recombinant polymerase of the invention was derived). For example, branching fraction, a reaction rate constant, $k_{off}$, $k_{cat}$, $K_m$, $V_{max}$, $k_{cat}/K_m$, $V_{max}/K_m$, $k_{pol}$, and/or $K_d$ of the recombinant DNA polymerase for the nucleotide (or analog) or template nucleic acid can be determined. The enzyme perfection metric $k_{cat}/K_m$ is also a useful measure, e.g., for assessing branch rate. $k_{cat}/K_m$ is a measure of substrate binding that leads to product formation (and, thus, includes terms defining binding $K_d$ and inversely predicts branching fraction formation).

As is well-known in the art, for enzymes obeying simple Michaelis-Menten kinetics, kinetic parameters are readily derived from rates of catalysis measured at different substrate concentrations. The Michaelis-Menten equation, $V=V_{max}[S]([S]+K_m)^{-1}$, relates the concentration of uncombined substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V).

For many enzymes, $K_m$ is equal to the dissociation constant of the enzyme-substrate complex and is thus a measure of the strength of the enzyme-substrate complex. For such an enzyme, in a comparison of $K_m$ values, a lower $K_m$ represents a complex with stronger binding, while a higher Km represents a complex with weaker binding. The ratio $k_{cat}/K_m$, sometimes called the specificity constant, can represent the apparent rate constant for combination of substrate with free enzyme. Under some conditions the specificity constant correlates with branching. For example, where there is a fixed on rate ($k_1$), an increase in the specificity constant will correlate with a decrease in the amount of branching.

The value $k_{cat}$ (also called the turnover number of the enzyme) can be determined if the total enzyme concentration ($[E_T]$, i.e., the concentration of active sites) is known, since $V_{max}=k_{cat}[E_T]$. For situations in which the total enzyme concentration is difficult to measure, the ratio $V_{max}/K_m$ is often used instead as a measure of efficiency. $K_m$ and $V_{max}$ can be determined, for example, from a Lineweaver-Burk plot of 1/V against 1/[S], where the y intercept represents $1/V_{max}$, the x intercept $-1/K_m$, and the slope $K_m/V_{max}$, or from an Eadie-Hofstee plot of V against V/[S], where the y intercept represents $V_{max}$, the x intercept $V_{max}/K_m$, and the slope $-K_m$. Software packages such as KinetAsyst™ or Enzfit (Biosoft, Cambridge, UK) can facilitate the determination of kinetic parameters from catalytic rate data.

For enzymes such as polymerases that have multiple substrates, varying the concentration of only one substrate while holding the others in suitable excess (e.g., effectively constant) concentration typically yields normal Michaelis-Menten kinetics.

Details regarding $k_{off}$ determination are described above. In general, the dissociation rate can be measured in any manner that detects the polymerase/DNA complex over time. This includes stopped-flow spectroscopy, or even simply by taking aliquots over time and testing for polymerase activity on the template of interest. Free polymerase is captured with a polymerase trap after dissociation, e.g., by incubation in the presence of heparin or an excess of competitor DNA (e.g., nonspecific salmon sperm DNA, or the like).

In one embodiment, using pre-steady-state kinetics, the nucleotide concentration dependence of the rate constant $k_{obs}$ (the observed first-order rate constant for dNTP incorporation) provides an estimate of the $K_m$ for a ground state binding and the maximum rate of polymerization ($k_{pol}$). The $k_{obs}$ is measured using a burst assay. The results of the assay are fitted with the Burst equation; Product=$A[1-\exp(-k_{obs}*t)]+k_{ss}*t$ where A represents amplitude an estimate of the concentration of the enzyme active sites, $k_{ss}$ is the observed steady-state rate constant and t is the reaction incubation time. The $K_m$ for dNTP binding to the polymerase-DNA complex and the $k_{pol}$ calculated by fitting the dNTP concentration dependent change in the $k_{obs}$ using the equation $k_{obs}=(k_{pol}*[S])*(K_m+[S])^{-1}$ where [S] is the substrate concentration. Results are optionally obtained from a rapid-quench experiment (also called a quench-flow measurement), for example, based on the methods described in Johnson (1986) "Rapid kinetic analysis of mechanochemical adenosinetriphosphatases" Methods Enzymol. 134:677-705, Patel et al. (1991) "Pre-steady-state kinetic analysis of processive DNA replication including complete characterization of an exonuclease-deficient mutant" Biochemistry 30(2):511-25, and Tsai and Johnson (2006) "A new paradigm for DNA polymerase specificity" Biochemistry 45(32):9675-87.

Parameters such as rate of binding of a nucleotide analog or template by the recombinant polymerase, rate of product release by the recombinant polymerase, or branching rate of the recombinant polymerase can also be determined, and optionally compared to that of a parental polymerase (e.g., a corresponding wild-type polymerase).

For a more thorough discussion of enzyme kinetics, see, e.g., Berg, Tymoczko, and Stryer (2002) *Biochemistry, Fifth Edition*, W. H. Freeman; Creighton (1984) *Proteins: Structures and Molecular Principles*, W. H. Freeman; and Fersht (1985) *Enzyme Structure and Mechanism, Second Edition*, W. H. Freeman.

Affinity Tags and Other Optional Polymerase Features

The recombinant DNA polymerase optionally includes additional features exogenous or heterologous to the polymerase. For example, the recombinant polymerase optionally includes one or more exogenous affinity tags, e.g., purification or substrate binding tags, such as a polyhistidine tag sequence, a 6 His tag sequence, a GST tag, an HA tag sequence, a plurality of 6 His tag sequences, a plurality of GST tags, a plurality of HA tag sequences, a SNAP-tag, a c-myc tag, a c-myc fusion, or the like. These and other features useful in the context of binding a polymerase to a surface are optionally included, e.g., to orient and/or protect the polymerase active site when the polymerase is bound to a surface. Other useful features include recombinant dimer domains of the enzyme, and, e.g., large extraneous polypeptide domains coupled to the polymerase distal to the active site. For example, for Φ29, the active site is in the C terminal region of the protein, and added surface binding elements (extra domains, His tags, etc.) are typically located in the N-terminal region to avoid interfering with the active site when the polymerase is coupled to a surface.

In general, surface binding elements and purification tags that can be added to the polymerase (recombinantly or, e.g., chemically) include, e.g., polyhistidine tags, HIS-6 tags, biotin, avidin, GST sequences, modified GST sequences, e.g., that are less likely to form dimers, biotin ligase recognition (BiTag) sequences, S tags, SNAP-tags, enterokinase sites, thrombin sites, antibodies or antibody domains, antibody fragments, antigens, receptors, receptor domains, receptor fragments, ligands, dyes, acceptors, quenchers, or combinations thereof.

Multiple surface binding domains can be added to orient the polypeptide relative to a surface and/or to increase binding of the polymerase to the surface. By binding a surface at two or more sites, through two or more separate tags, the polymerase is held in a relatively fixed orientation with respect to the surface. Additional details on fixing a polymerase to a surface, attaching tags, and the like are found in WO 2007/075987 ACTIVE SURFACE COUPLED POLYMERASES by Hanzel et al., and WO 2007/076057 PROTEIN ENGINEERING STRATEGIES TO OPTIMIZE ACTIVITY OF SURFACE ATTACHED PROTEINS by Hanzel et al. Further details on attaching tags is available in the art. See, e.g., U.S. Pat. Nos. 5,723,584 and 5,874,239 for additional information on attaching biotinylation peptides to recombinant proteins.

Making and Isolating Recombinant Polymerases

Generally, nucleic acids encoding a polymerase of the invention can be made by cloning, recombination, in vitro synthesis, in vitro amplification and/or other available methods. A variety of recombinant methods can be used for expressing an expression vector that encodes a polymerase of the invention, e.g., a mutant polymerase that, without being bound to a particular theory, decreases reaction rate, increases closed complex stability, or that includes a nucleotide complementarity/active site access feature that makes the enzyme more efficient at using the nucleotide (decreasing branching fraction). Recombinant methods for making nucleic acids, expression and isolation of expressed products are well known and described in the art. Optionally, when modifying the active site, features are selected (e.g., by modeling, though random approaches can also be used) that improve steric access of the nucleotide analog to the active site and/or that improves charge-charge or hydrophobic interactions between a given nucleotide analog and the polymerase target. Methods for making and selecting mutations in the active site of polymerases, including for modifying steric features in or near the active site to permit improved access by nucleotide analogs are found, e.g., in WO 2007/076057 POLYMERASES FOR NUCLEOTIDE ANALOGUE INCORPORATION by Hanzel et al., and WO 2008/051530 POLYMERASE ENZYMES AND REAGENTS FOR ENHANCED NUCLEIC ACID SEQUENCING by Rank et al.

Additional useful references for mutation, recombinant and in vitro nucleic acid manipulation methods (including cloning, expression, PCR, and the like) include Berger and Kimmel, *Guide to Molecular Cloning Techniques, Methods in Enzymology volume* 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley); Chen et al. (ed) *PCR Cloning Protocols, Second Edition* (Methods in Molecular Biology, volume 192) Humana Press; and in Viljoen et al. (2005) *Molecular Diagnostic PCR Handbook* Springer, ISBN 1402034032.

In addition, a plethora of kits are commercially available for the purification of plasmids or other relevant nucleic acids from cells, (see, e.g., EasyPrep™, FlexiPrep™, both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

In addition, systems of orthogonal components are available that can incorporate any of a variety of unnatural (non-natural) amino acids into a recombinant protein (e.g., polymerase of the invention). In brief, a cell or other translation system (e.g., an in vitro translation system) is constructed that includes an orthogonal tRNA ("OtRNA," a tRNA, not recognized by the cell's endogenous translation machinery, such as an amber or 4-base tRNA) and an orthogonal tRNA synthetase ("ORS," a synthetase that does not aminoacylate any endogenous tRNA of the cell but which can aminoacylate the OtRNA in response to a selector codon). A nucleic acid encoding the enzyme is constructed to include a selector codon at a selected position that is specifically recognized by the OtRNA. The ORS specifically incorporates an unnatural amino acid with a desired chemical functionality at one or more selected sites. This chemical functional group can be unique as compared to those ordinarily found on amino acids. These are coupled to the coupling domains through appropriate chemical linkages. Further information on orthogonal systems can be found, e.g., in Wang et al. (2001) Science 292:498-500, Chin et al. (2002) Journal of the American Chemical Society 124:9026-9027, Chin and Schultz (2002) Chem Bio Chem 11:1135-1137, Chin et al. (2002) PNAS 99:11020-11024, and Wang and Schultz (2002) Chem. Comm., 1-10. See also, International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; and WO 2005/007624, filed Jul. 7, 2004.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

A variety of protein isolation and detection methods are known and can be used to isolate polymerases, e.g., from recombinant cultures of cells expressing the recombinant polymerases of the invention. A variety of protein isolation and detection methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997); *Bioseparation of Proteins*, Academic Press, Inc.; Bollag et al. (1996), Satinder Ahuja ed., *Handbook of Bioseparations*, Academic Press (2000).

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc., and John Wiley & Sons, Inc., supplemented through 2004).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Coupling of Labels to the Polymerase

The labels can be coupled to the proteins by any suitable reaction, including site-specifically introducing a reporter group(s) by total synthesis, semi-synthesis, or gene fusions (see, for example, Adams et al., Nature 39:694-697, 1991; Brune et al., Biochemistry 33:8262-8271, 1994; Gilardi et al., Anal. Chem. 66:3840-3847, 1994; Godwin et al., J. Am. Chem. Soc. 118:6514-6515, 1996; Marvin et al., Proc. Natl. Acad. Sci. U.S.A. 94:4366-4371, 1997; Post et al., J. Biol. Chem. 269:12880-12887, 1994; Romoser, J. Biol. Chem. 272:13270-13274, 1997; Thompson et al., J. Biomed. Op. 1:131-137, 1996; Walkup et al., J. Am. Chem. Soc. 119:5445-5450, 1997). For example, fluorophore conjugation to cysteine-substituted bPBPs can be performed. Thiol-reactive fluorophores such as those available from Molecular Probes (Eugene, Oreg.), e.g. 5-iodoacetamidofluorescein (fluorescein); N-(1-pyrene) iodoacetamide (pyrene); N,N'-dimethyl-N-(iodoacetyl)-N'-(7-nitrobenz-2-oxa-1,3-diazol-4-yl)ethylenediamine (NBD); N-((2-(iodoacetoxy)ethyl)-N-methyl) amino-7-nitrobenz-2-oxa-1,3-diazole (NBDE); and 6-acryloyl-2-dimethylaminonaphthalene (acrylodan) can be used. Labels can be attached using Fluorescein Arsenical Hairpin binder technology (FlAsH/tetracysteine), Machleidt et al. Methods in Molecular Biology 356, 209-220, 2006, doi/10.1385/1-59745-217-3:209. Labels can be attached, for example using HaloTag fusion technology available through Promega or using site-specific protein labeling using transpeptidation of a functionalized oligoglycine peptide, see Curr. Protoc. Protein Sci., April 2009, Chapter 15:Unit 15.3. Quantum dots can be linked to proteins, for example via polyhistidine motifs. See, e.g. Dif et al., J. Am. Chem. Soc., 131(41), 14738-46, 2009.

Template Nucleic Acids

The template nucleic acids of the invention can comprise any suitable polynucleotide, including double-stranded DNA, single-stranded DNA, single-stranded DNA hairpins, DNA/RNA hybrids, RNAs with a recognition site for binding of the polymerizing agent, and RNA hairpins. Further, target polynucleotides may be a specific portion of a genome of a cell, such as an intron, regulatory region, allele, variant or mutation; the whole genome; or any portion thereof. In other embodiments, the target polynucleotides may be mRNA, tRNA, rRNA, ribozymes, antisense RNA or RNAi. The target polynucleotide may be of any length, such as at between about 10 bases and about 100,000 bases, or between about 100 bases and 10,000 bases.

The template nucleic acids of the invention can include unnatural nucleic acids such as PNAs, modified oligonucleotides (e.g., oligonucleotides comprising nucleotides that are not typical to biological RNA or DNA, such as 2'-O-methylated oligonucleotides), modified phosphate backbones and the like. A nucleic acid can be e.g., single-stranded or double-stranded.

Systems

The invention includes systems for sequencing of nucleic acid templates. The systems provide for concurrently sequencing a plurality of nucleic acid templates. The system can incorporate all of the reagents and methods described herein, and provides the instrumentation required for containing the sample, illuminating the sample with excitation light, detecting light emitted from the sample during sequencing to produce intensity versus time data from the labeled nucleotides and from the label indicative of enzyme conformation, and determining the sequence of a template using the intensity versus time data.

The system for sequencing generally comprises a substrate having a plurality of single polymerase enzyme complexes each comprising a polymerase enzyme, a nucleic acid template, and a primer. The polymerase enzyme comprises a label having a signal that changes when the enzyme undergoes a conformational change. The substrate is in contact with sequencing reagents which provide the components required for the polymerase enzyme to add labeled nucleotides or nucleotide analogs while the addition of the nucleotide analogs is observed. The sequencing reagents include two or more types of nucleotides or nucleotide analogs, each nucleotide or nucleotide analog labeled with a different label. The polymerase sequentially adds nucleotides or nucleotide analogs to the growing strand, which extends from the primer. Each added nucleotide or nucleotide analog is complementary to the corresponding base on the template nucleic acid, such that the portion of the growing strand that is produced is complementary to the template.

The system comprises illumination optics for illuminating the enzyme complexes. The illumination optics illuminate the complexes in a wavelength range that will excite the labels on the nucleotides or nucleotide analog and which will excite the labels on the polymerase enzyme that are sensitive to changes in conformation.

The system further comprises detection optics for observing signals from the labeled nucleotides or nucleotide analogs and signals from the labeled enzyme during the enzyme mediated addition. The detection optics observe a plurality of single polymerase enzyme complexes concurrently, observing the nucleotide or nucleotide analog additions for each of them. For each of the observed polymerase enzyme complexes, the detection optics concurrently observe the signals from each of the labeled nucleotides or nucleotide analogs and the signals from the labeled enzyme that are indicative of enzyme conformation.

The system also comprise a computer configured to determine the type of the nucleotides or nucleotide analog that is added to the growing strand using the observed signal from the label of the nucleotide or nucleotide analogs; whereby observed signals from the labeled polymerase enzyme are used to indicate whether a type of nucleotide or nucleotide analog is incorporated into the growing strand. The computer generally receives information regarding the observed signals from the detection optics in the form of signal data. The computer stores, processes, and interprets the signal data, using the signal data in order to produce a sequence of base calls. The base calls represent the computers estimate of the sequence of the template from the signal data received combined with other information given to the computer to assist in the sequence determination.

Figure 9:
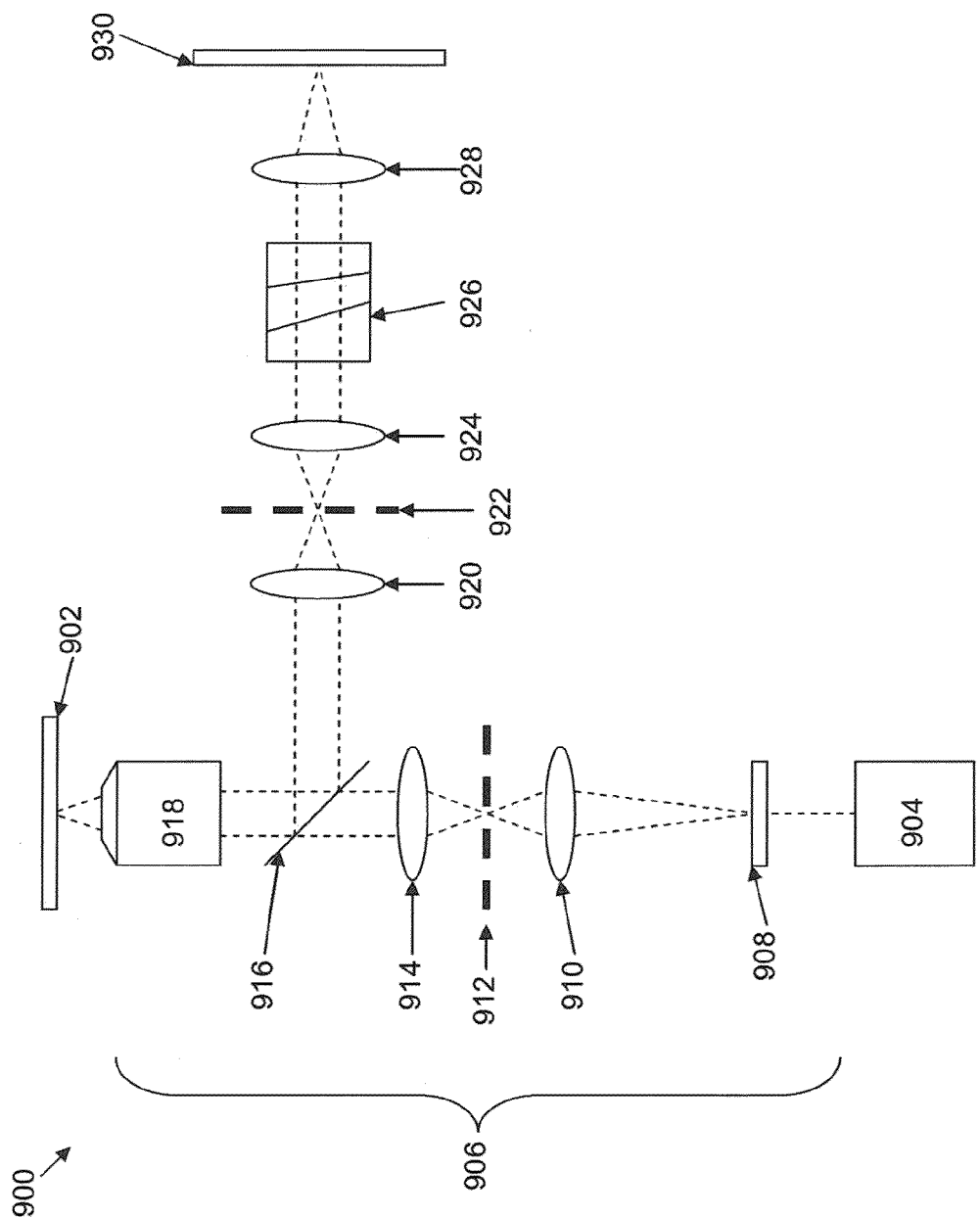
FIG. 9 is a schematic drawing of a system of the invention.

One example of such system is illustrated in FIG. 9. As shown, the system 900, includes a reaction array, such as a zero-mode waveguide array 902 upon which a number of discrete reaction regions are arrayed. Within the zero-mode waveguides are immobilized single polymerase enzyme complexes having labels indicative of enzyme conformation. The zero-mode waveguides are also exposed to sequencing reagents including labeled nucleotides or nucleotide analogs, for example four differentially labeled nucleotides or nucleotide analogs. In the case of a zero mode waveguide array, large numbers of zero mode waveguides are typically provided arrayed in rows and columns on the substrate. Within the various ZMWs are provided reactants of interest for a given analysis. For example, in the context of nucleic acid sequencing by synthesis, a sequencing complex that includes a template nucleic acid sequence, a complementary primer sequence, a nucleic acid polymerase enzyme, and a reaction mixture of nucleotides or nucleotide analogs required for primer extension are provided with the ZMW (See, e.g., FIG. 4). ZMW arrays can be fabricated at ultra high density, providing anywhere from 1000 ZMWs per cm2, to 1,000,000 ZMWs per cm2, or more. Thus, at any given time, it may be desirable to analyze the reactions occurring in from 100, 1000, 3000, 5000, 10,000, 20,000, 50,000, 100,000 or 1 Million, 10 Million or more ZMWs or other reaction regions within a single analytical system or even on a single substrate.

As shown, the system includes a source of excitation radiation for exciting fluorescent reactants in the reaction regions, such as laser 904. An optical train 906 delivers excitation radiation from laser 904 to the ZMW array or substrate 902. The optical train also collects fluorescent signals from the various ZMWs on the array, and conveys those signals to a detector, such as EMCCD 930. The optical train 906 includes a multiplex component, such as diffractive optical element (DOE) 908 (also referred to as a holographic optical element or HOE), that converts a single excitation beam to large number of discrete excitation beams that will be targeted in an array of illumination spots that correspond to the location of the ZMWs on the array 902. The multiple beams are passed through a dichroic 916 that is selected to pass excitation light and reflect the fluorescence from the array 902. Prior to passing through the dichroic 916, the illumination beams may be passed through a confocal filter 912 which may have associated with it a pair of focusing lenses, e.g., lenses 910 and 914, in order to focus these beams through the confocal pinhole(s). The excitation light that is passed through dichroic 916 is then focused in a targeted pattern onto the plane of the array 902 via objective lens 918.

Fluorescent signals from array 902 are then collected by the objective lens 918, and passed to dichroic 916, which reflects the fluorescent signals toward detector 930. The signals from the discrete ZMWs on the array are then passed through a spatial filter, such as confocal mask 922, to reduce background noise, such as photoluminescence, out of focal plane autofluorescence or scattered light, which again typically has associated with it a pair of focusing lenses, e.g., lenses 920 and 924. The signals can then be passed through a dispersive optical element, such as wedge prism 926, that differentially directs light of differing spectral characteristics, allowing for distinction of different fluorescent signals based upon the location upon the detector, upon which they impinge. The differentially directed signal components are then directed through additional focusing optics, e.g., focusing lens 928, and ultimately impact the EMCCD detector 930. As noted, the position on the detector upon which a given signal is incident can then be indicative of (1) the originating ZMW in the array, and (2) the spectral characteristics of the signal component, which is used, for example, to identify the type of fluorescently labeled nucleotide analog incorporated in an extension reaction and that is used to monitor the label on the enzyme which is indicative of enzyme conformation.

Optical illumination and detections systems which can be used with the present invention are described, for example in U.S. patent application Ser. No. 12/351,173 filed Jan. 9, 2009, U.S. patent application Ser. No. 11/901,273 filed Sep. 14, 2007, U.S. patent application Ser. No. 12/151,979 filed May 9, 2008, U.S. patent application Ser. No. 12/079,944 filed Mar. 27, 2008, and U.S. patent application Ser. No. 11/849,157 filed Aug. 31, 2007, which are incorporated herein by reference for all purposes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

Optical Confinements—Zero-Mode Waveguides

In some embodiments of the methods and systems of the invention, optical confinements are used to enhance the ability to concurrently observe multiple single polymerase enzyme complexes simultaneously. In general, optical confinements are disposed upon a substrate and used to provide electromagnetic radiation to or derive such radiation from only very small spaces or volumes. Such optical confinements may comprise structural confinements, e.g., wells, recesses, conduits, or the like, or they may comprise optical processes in conjunction with other components, to provide illumination to or derive emitted radiation from only very small volumes. Examples of such optical confinements include systems that utilize, e.g., total internal reflection (TIR) based optical systems whereby light is directed through a transparent portion of the substrate at an angle that yields total internal reflection within the substrate.

The substrates of the invention are generally rigid, and often planar, but need not be either. Where the substrate comprises an array of optical confinements, the substrate will generally be of a size and shape that can interface with optical instrumentation to allow for the illumination and for the measurement of light from the optical confinements. Typically, the substrate will also be configured to be held in contact with liquid media, for instance containing reagents and substrates and/or labeled components for optical measurements.

Where the substrates comprise arrays of optical confinements, the arrays may comprise a single row or a plurality of rows of optical confinement on the surface of a substrate, where when a plurality of lanes are present, the number of lanes will usually be at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to Eosin a grid, or to form a circular, elliptical, oval, conical, rectangular, triangular, or polyhedral pattern. To minimize the nearest-neighbor distance between adjacent optical confinements, a hexagonal array is sometimes preferred.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter plate wherein each micro well of the plate contains a subject array of optical confinements.

In accordance with the invention, arrays of confinements, e.g., zero mode waveguides, are provided in arrays of more than 100, more than 1000, more than 10,000, more that 100,000, or more than 1,000,000 separate waveguides on a single substrate. In addition, the waveguide arrays typically comprise a relatively high density of waveguides on the surface of the substrate. Such high density typically includes waveguides present at a density of greater than 10 zero mode waveguides per mm2, preferably, greater than 100 waveguides per mm2 of substrate surface area, and more preferably, greater than 500 or even 1000 waveguides per mm2 and in many cases up to or greater than 100,000 waveguides per mm mm2. Although in many cases, the waveguides in the array are spaced in a regular pattern, e.g., in 2, 5, 10, 25, 50 or 100 or more rows and/or columns of regularly spaced waveguides in a given array, in certain preferred cases, there are advantages to providing the organization of waveguides in an array deviating from a standard row and/or column format. In preferred aspects, the substrates include zero mode waveguides as the optical confinements to define the discrete reaction regions on the substrate.

The optical confinements can be zero-mode-waveguides. Zero mode waveguides have been described in, e.g., U.S. Pat. No. 6,917,726, the full disclosure of which is incorporated herein by reference in its entirety for all purposes. Generally, such waveguides comprise a core disposed through a cladding layer, which in the case of applications to reactions, comprises an aperture disposed through the cladding layer that can receive the reactants to be monitored. Typically, the aperture has at least one cross-sectional dimension, e.g., diameter, which is sufficiently small that light entering the waveguide is prevented in some measure from propagating through the core, effectively resulting in a very small portion of the core and its contents being illuminated, and/or emitting optical signals that exit the core. In the case of optical signals (and excitation radiation), the waveguide cores will typically be between about 1 nm and about 300 nm, between about 10 and about 200 nm, or between about 50 and about 150 nm in diameter where light in the visible range is used.

The overall size of the array of optical confinements can generally range from a few nanometers to a few millimeters in thickness, and from a few millimeters to 50 centimeters in width and/or length. Arrays may have an overall size of about few hundred microns to a few millimeters in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements may be placed close to each other relative to the incident wavelength.

The individual confinement in the array can provide an effective observation volume less than about 1000 zeptoliters, less than about 900, less than about 200, less than about 80, less than about 10 zeptoliters. Where desired, an effective observation volume less than 1 zeptoliter can be provided. In a preferred aspect, the individual confinement yields an effective observation volume that permits resolution of individual molecules, such as enzymes, present at or near a physiologically relevant concentration. The physiologically relevant concentrations for many biochemical reactions range from micro-molar to millimolar because most of the enzymes have their Michaelis constants in these ranges. Accordingly, preferred array of optical confinements has an effective observation volume for detecting individual molecules present at a concentration higher than about 1 micromolar ($\mu$M), or more preferably higher than 50 $\mu$M, or even higher than 100 $\mu$M.

As zero-mode-waveguide can provide an optical guide in which the majority of incident radiation is attenuated, preferably more than 80%, more preferably more than 90%, even more preferably more than 99% of the incident radiation is attenuated. As such high level of attenuation, no significant propagating modes of electromagnetic radiation exist in the guide. Consequently, the rapid decay of incident electromagnetic radiation at the entrance of such guide provides an extremely small observation volume effective to detect single-molecules, even when they are present at a concentration as high as in the micromolar range.

The zero-mode-waveguide of the present invention typically comprises a cladding surrounding a core (i.e., partially or fully), wherein the cladding is configured to preclude propagation of electromagnetic energy of a wavelength higher than the cutoff wavelength longitudinally through the core of the zero-mode waveguide. The cladding is typically made of materials that prevent any significant penetration of the electric and the magnetic fields of an electromagnetic radiation that is opaque and/or reflective materials. Suitable materials for fabricating the cladding include but are not limited to metals, metal oxides, alloys, and semi-conducting materials, and any combination thereof.

The internal cavity (i.e., the core) surrounded by the cladding may adopt a convenient size, shape or volume so long as propagating modes of electromagnetic radiation in the guide is effectively prevented. The core typically has a lateral dimension less than the cutoff wavelength ($\lambda c$). For a circular guide of diameter d and having a clad of perfect conductor, $\lambda c$ is approximately 1.7 times d. The cross sectional area of the core may be circular, elliptical, oval, conical, rectangular, triangular, polyhedral, or in any other shape. Although uniform cross sectional area is generally preferred, the cross sectional area may vary at any given depth of the guide if desired.

The optical performance of the ZMW can be enhanced by incorporation within a micromirror structure on the substrate. The incorporation of micromirrors and other methods of improving optical performance in multiplex systems are describe in copending U.S. patent application Ser. No. 12/567,526, filed Sep. 25, 2009.

In the context of chemical or biochemical analyses within ZMWs as well as other optical confinements, it is generally desirable to ensure that the reactions of interest are taking place within the optically interrogated portions of the confinement, at a minimum, and preferably such that only the reactions of a single molecule is occurring within an interrogated portion of an individual confinement. A number of methods may generally be used to provide individual molecules within the observation volume. A variety of these are described in co-pending U.S. patent application Ser. No. 11/240,662, filed Sep. 30, 2005, incorporated herein by reference in its entirety for all purposes, which describes, inter alia, modified surfaces that are designed to immobilize individual molecules to the surface at a desired density, such that approximately one, two, three or some other select number of molecules would be expected to fall within a given observation volume. Typically, such methods utilize dilution techniques to provide relatively low densities of coupling groups on a surface, either through dilution of such groups on the surface or dilution of intermediate or final coupling groups that interact with the molecules of interest, or combinations of these.

Base Calling and Sequence Determination

Figure 10:
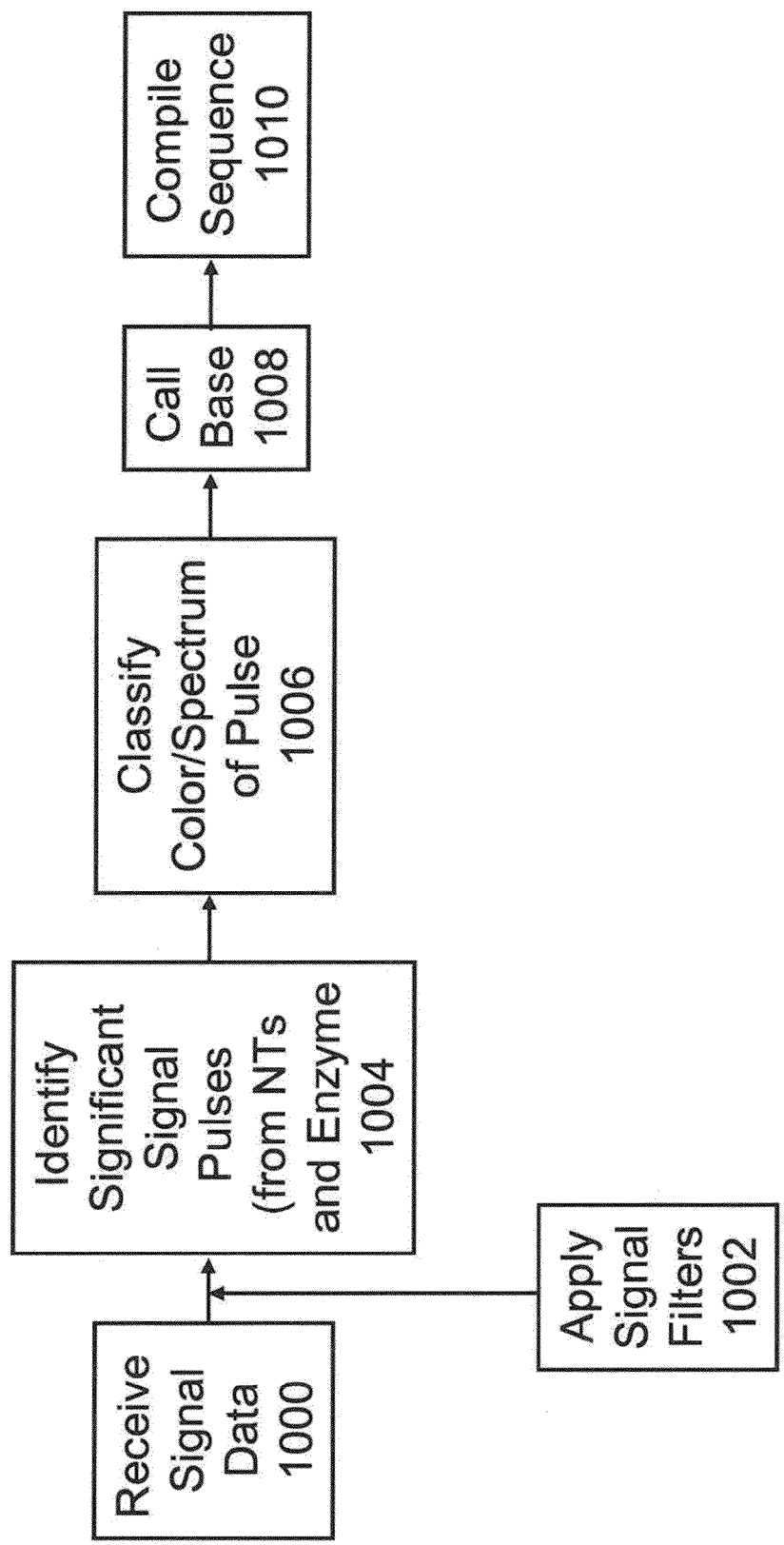
FIG. 10 is a flow chart describing a process of base calling and sequence determination.

The systems and methods of the inventions can result in improved sequence determination and improved base calling by using information from the labeled nucleotides along with concurrent information from the labeled protein indicating the conformation of the protein. A general flow chart illustrating an embodiment of a base calling and sequence determination process using such signal data is provided in FIG. 10. In general, signal data is received by the processor at step 1000. The information received by the processor can come directly from the detection optics, or the signal from the detection optics can be treated by other processors before being received by the processor at step 1000. A number of initial calibrations operations may be applied at step 1002. Some of these initial calibration steps may be performed just once at the beginning of a run or on a more continuous basis during the run. These initial calibration steps can include such things as centroid determination, alignment, gridding, drift correction, initial background subtraction, noise parameter adjustment, frame-rate adjustment, etc. Some of these initial calibration steps, such as binning, may involve communication from the processor back to the detector/camera, as discussed further below.

Generally, some type of spectral trace determination/spectral trace extraction/spectral filters are applied to the initial signal data at step 1002. Some or all of this filter step may optionally be carried out at a later point in the process, e.g., after the pulse identification step 1004. The spectral trace extraction/spectral filters may include a number of noise reduction and other filters as set forth elsewhere herein. Spectral trace determination is performed at this stage for many of the example systems discussed herein because the initial signal data received are the light levels, or photon counts, captured by a series of adjacent pixel detectors. For example, in one example system, 14 pixels (or intensity levels) from 14 positions are captured for an individual wave-guide at each frame. Light of different frequencies or spectrum will fall on more than one of the 14 positions and there is generally some overlap and possibly substantial overlap. According to specific embodiments of the invention, spectral trace extraction may be performed using various analysis, as discussed below, that provide the highest signal-to-noise ratio for each spectral trace.

As an alternative to a spectral trace determination, methods of the invention may also analyze a single signal derived from the intensity levels at the multiple pixel positions (this may be referred to as a summed spectral signal or a gray-scale spectral signal or an intensity level signal). In many situations, it has been found that spectral extraction, however, provides better SNR and therefore pulse detection when extracted spectral traces are analyzed for pulses somewhat separately. In further embodiments, a method according to the invention may analyze the multiple captured pixel data using a statistical model such as a Hidden Markov Model. In present systems, however, determining multiple (e.g., four) spectral traces from the initial signal data has proven a preferred method.

Whether the signal from the labels on the nucleotides or the label or labels on the polymerase can be categorized as a significant signal pulse or event is determined at step 1004. In some example systems, because of the small number of photons available for detection and because of the speed of detection, various statistical analysis techniques may be performed in determining whether a significant pulse has been detected.

If the signal is identified as a significant pulse or signal event at step 1004, a further optional spectral profile comparison may be performed to verify the spectral assignment. This spectral profile comparison is optional in embodiments where spectral traces are determined prior to or during pulse identification. Once a color is assigned to a given incorporation signal, that assignment is used to call either the base incorporated, or its complement in the template sequence, at step 1008. In order to make this determination, the signals from the channel corresponding to the label on the enzyme which is sensitive to enzyme conformation is used to assess whether a pulse from a nucleotide label corresponds to an incorporation event. The compilation of called bases is then subjected to additional processing at step 1010, to provide linear sequence information, e.g., the successive sequence of nucleotides in the template sequence, assemble sequence fragments into longer contigs, or the like.

As noted above, the signal data is input into the processing system, e.g., an appropriately programmed computer or other processor. Signal data may input directly from a detection system, e.g., for real time signal processing, or it may be input from a signal data storage file or database. In some cases, e.g., where one is seeking immediate feedback on the performance of the detection system, adjusting detection or other experimental parameters, real-time signal processing will be employed. In some embodiments, signal data is stored from the detection system in an appropriate file or database and is subject to processing in post reaction or non-real time fashion.

The signal data used in conjunction with the present invention may be in a variety of forms. For example, the data may be numerical data representing intensity values for optical signals received at a given detector or detection point of an array based detector. Signal data may comprise image data from an imaging detector, such as a CCD, EMCCD, ICCD or CMOS sensor. In either event, signal data used according to specific embodiments of the invention generally includes both intensity level information and spectral information. In the context of separate detector elements, such spectral information will generally includes identification of the location or position of the detector portion (e.g., a pixel) upon which an intensity is detected. In the context of image data, the spectral image data will typically be the data derived from the image data that correlates with the calibrated spectral image data for the imaging system and detector when the system includes spectral resolution of overall signals. The spectral data may be obtained from the image data that is extracted from the detector, or alternatively, the derivation of spectral data may occur on the detector such that spectral data will be extracted from the detector.

For the sequencing methods described above, there will be a certain amount of optical signal that is detected by the detection system that is not the result of a signal from an incorporation event. Such signal will represent "noise" in the system, and may derive from a number of sources that may be internal to the monitored reaction, internal to the detection system and/or external to all of the above. Examples of noise internal to the reaction being monitored includes, e.g.: presence of fluorescent labels that are not associated with a detection event, e.g., liberated labels, labels associated with unincorporated bases in diffused in solution, bases associated with the complex but not incorporated; presence of multiple complexes in an individual observation volume or region; non-specific adsorption of dyes or nucleotides to the substrate or enzyme complex within an observation volume; contaminated nucleotide analogs, e.g., contaminated with other fluorescent components; other reaction components that may be weakly fluorescent; spectrally shifting dye components, e.g., as a result of reaction conditions; and the like. The use of information from the label on the polymerase sensitive to enzyme conformation provides a way of reducing or eliminating sources of noise, thereby improving the signal to noise of the system, and improving the quality of the base calls and associated sequence determination.

Sources of noise internal to the detection system, but outside of the reaction mixture can include, e.g., reflected excitation radiation that bleeds through the filtering optics; scattered excitation or fluorescent radiation from the substrate or any of the optical components; spatial cross-talk of adjacent signal sources; auto-fluorescence of any or all of the optical components of the system; read noise from the detector, e.g., CCDs, gain register noise, e.g., for EMCCD cameras, and the like. Other system derived noise contributions can come from data processing issues, such as background correction errors, focus drift errors, autofocus errors, pulse frequency resolution, alignment errors, and the like. Still other noise contributions can derive from sources outside of the overall system, including ambient light interference, dust, and the like.

These noise components contribute to the background photons underlying any signal pulses that may be associated with an incorporation event. As such, the noise level will typically form the limit against which any signal pulses may be determined to be statistically significant.

Identification of noise contribution to overall signal data may be carried out by a number of methods, including, for example, signal monitoring in the absence of the reaction of interest, where any signal data is determined to be irrelevant. Alternatively, and preferably, a baseline signal is estimated and subtracted from the signal data that is produced by the system, so that the noise measurement is made upon and contemporaneously with the measurements on the reaction of interest. Generation and application of the baseline may be carried out by a number of means, which are described in greater detail below.

In accordance with the present invention, signal processing methods distinguish between noise, as broadly applied to all non-significant pulse based signal events, and significant signal pulses that may, with a reasonable degree of confidence, be considered to be associated with, and thus can be tentatively identified as, an incorporation event. In the context of the present invention, a signal event is first classified as to whether it constitutes a significant signal pulse based upon whether such signal event meets any of a number of different pulse criteria. Once identified or classified as a significant pulse, the signal pulse may be further assessed to determine whether the signal pulse constitutes an incorporation event and may be called as a particular incorporated base. As will be appreciated, the basis for calling a particular signal event as a significant pulse, and ultimately as an incorporation event, will be subject to a certain amount of error, based upon a variety of parameters as generally set forth herein. As such, it will be appreciated that the aspects of the invention that involve classification of signal data as a pulse, and ultimately as an incorporation event or an identified base, are subject to the same or similar errors, and such nomenclature is used for purposes of discussion and as an indication that it is expected with a certain degree of confidence that the base called is the correct base in the sequence, and not as an indication of absolute certainty that the base called is actually the base in a given position in a given sequence.

One such signal pulse criterion is the ratio of the signals associated with the signal event in question to the level of all background noise ("signal to noise ratio" or "SNR"), which provides a measure of the confidence or statistical significance with which one can classify a signal event as a significant signal pulse. In distinguishing a significant pulse signal from systematic or other noise components, the signal generally must exceed a signal threshold level in one or more of a number of metrics, including for example, signal intensity, signal duration, temporal signal pulse shape, pulse spacing, and pulse spectral characteristics.

By way of a simplified example, signal data may be input into the processing system. If the signal data exceeds a signal threshold value in one or more of signal intensity and signal duration, it may be deemed a significant pulse signal. Similarly, if additional metrics are employed as thresholds, the signal may be compared against such metrics in identifying a particular signal event as a significant pulse. As will be appreciated, this comparison will typically involve at least one of the foregoing metrics, and preferably at least two such thresholds, and in many cases three or all four of the foregoing thresholds in identifying significant pulses.

Signal threshold values, whether in terms of signal intensity, signal duration, pulse shape, spacing or pulse spectral characteristics, or a combination of these, will generally be determined based upon expected signal profiles from prior experimental data, although in some cases, such thresholds may be identified from a percentage of overall signal data, where statistical evaluation indicates that such thresholding is appropriate. In particular, in some cases, a threshold signal intensity and/or signal duration may be set to exclude all but a certain fraction or percentage of the overall signal data, allowing a real-time setting of a threshold. Again, however, identification of the threshold level, in terms of percentage or absolute signal values, will generally correlate with previous experimental results. In alternative aspects, the signal thresholds may be determined in the context of a given evaluation. In particular, for example, a pulse intensity threshold may be based upon an absolute signal intensity, but such threshold would not take into account variations in signal background levels, e.g., through reagent diffusion, that might impact the threshold used, particularly in cases where the signal is relatively weak compared to the background level. As such, in certain aspects, the methods of the invention determine the background fluorescence of the particular reaction in question, including, in particular, the contribution of freely diffusing dyes or dye labeled analogs into a zero mode waveguide, and set the signal threshold above that actual background by the desired level, e.g., as a ratio of pulse intensity to background fluorophore diffusion, or by statistical methods, e.g., 5 sigma, or the like. By correcting for the actual reaction background, such as fluorophore diffusion background, the threshold is automatically calibrated against influences of variations in dye concentration, laser power, or the like. By reaction background is meant the level of background signal specifically associated with the reaction of interest and that would be expected to vary depending upon reaction conditions, as opposed to systemic contributions to background, e.g., autofluorescence of system or substrate components, laser bleedthrough, or the like.

In particularly preferred aspects that rely upon real-time detection of incorporation events, identification of a significant signal pulse may rely upon a signal profile that traverses thresholds in both signal intensity and signal duration. For example, when a signal is detected that crosses a lower intensity threshold in an increasing direction, ensuing signal data from the same set of detection elements, e.g., pixels, are monitored until the signal intensity crosses the same or a different intensity threshold in the decreasing direction. Once a peak of appropriate intensity is detected, the duration of the period during which it exceeded the intensity threshold or thresholds is compared against a duration threshold. Where a peak comprises a sufficiently intense signal of sufficient duration, it is called as a significant signal pulse.

In addition to, or as an alternative to using the intensity and duration thresholds, pulse classification may employ a number of other signal parameters in classifying pulses as significant. Such signal parameters include, e.g., pulse shape, spectral profile of the signal, e.g., pulse spectral centroid, pulse height, pulse diffusion ratio, pulse spacing, total signal levels, and the like.

Either following or prior to identification of a significant signal pulse, signal data may be correlated to a particular signal type. In the context of the optical detection schemes used in conjunction with the invention, this typically denotes a particular spectral profile of the signal giving rise to the signal data. In particular, the optical detection systems used in conjunction with the methods and processes of the invention are generally configured to receive optical signals that have distinguishable spectral profiles, where each spectrally distinguishable signal profile may generally be correlated to a different reaction event. In the case of nucleic acid sequencing, for example, each spectrally distinguishable signal may be correlated or indicative of a specific nucleotide incorporated or present at a given position of a nucleic acid sequence. Consequently, the detection systems include optical trains that receive such signals and separate the signals based upon their spectra. The different signals are then directed to different detectors, to different locations on a single array based detector, or are differentially imaged upon the same imaging detector (See, e.g., U.S. Patent Publication No. 2007/0036511, which is incorporated herein by reference in its entirety for all purposes).

In the case of systems that employ different detectors for different signal spectra, assignment of a signal type (for ease of discussion, referred to hereafter as "color classification" or "spectral classification") to a given signal is a matter of correlating the signal pulse with the detector from which the data derived. In particular, where each separated signal component is detected by a discrete detector, a signal's detection by that detector is indicative of the signal classifying as the requisite color.

In preferred aspects, however, the detection systems used in conjunction with the invention utilize an imaging detector upon which all or at least several of the different spectral components of the overall signal are imaged in a manner that allows distinction between different spectral components. Thus, multiple signal components are directed to the same overall detector, but may be incident upon wholly or partly different regions of the detector, e.g., imaged upon different sets of pixels in an imaging detector, and give rise to distinguishable spectral images (and associated image data). As used herein, spectra or spectral image generally indicates a pixel image or frame (optionally data reduced to one dimension) that has multiple intensities caused by the spectral spread of an optical signal received from a reaction location.

In its simplest form, it will be understood that assignment of color to a signal event incident upon a group of contiguous detection elements or pixels in the detector would be accomplished in a similar fashion as that set forth for separate detectors. In particular, the position of the group of pixels upon which the signal was imaged, and from which the signal data is derived, is indicative of the color of the signal component. In particularly preferred aspects, however, spatial separation of the signal components may not be perfect, such that signals of differing colors are imaged on overlapping sets of pixels. As such, signal identification will generally be based upon the aggregate identity of multiple pixels (or overall image of the signal component) upon which a signal was incident.

Once a particular signal is identified as a significant pulse and is assigned a particular spectrum, the spectrally assigned pulse may be further assessed to determine whether the pulse can be called an incorporation event and, as a result, call the base incorporated in the nascent strand, or its complement in the template sequence. In order to make the determination of incorporation, the signal from the label on the enzyme sensitive to enzyme conformation is used. For example, where the signal from the enzyme corresponds to translocation, the observation of signals indicative of translocation before and after the signal from the nucleotide is used to indicate whether an observed peak associated with a nucleotide corresponds to an actual incorporation. Where the signal from the enzyme is measures an open-closed conformational change, the observation of a closed conformation concurrent with the signal from the nucleotide can be used as an indication that incorporation has occurred. In addition, calling of bases from color assigned pulse data will typically employ tests that again identify the confidence level with which a base is called. Typically, such tests will take into account the data environment in which a signal was received, including a number of the same data parameters used in identifying significant pulses, etc. For example, such tests may include considerations of background signal levels, adjacent pulse signal parameters (spacing, intensity, duration, etc.), spectral image resolution, and a variety of other parameters. Such data may be used to assign a score to a given base call for a color assigned signal pulse, where such scores are correlative of a probability that the base called is incorrect, e.g., 1 in 100 (99% accurate), 1 in 1000 (99.9% accurate), 1 in 10,000 (99.99% accurate), 1 in 100,000 (99.999% accurate), or even greater. Similar to PHRED or similar type scoring for chromatographically derived sequence data, such scores may be used to provide an indication of accuracy for sequencing data and/or filter out sequence information of insufficient accuracy.

Once a base is called with sufficient accuracy, subsequent bases called in the same sequencing run, and in the same primer extension reaction, may then be appended to each previously called base to provide a sequence of bases in the overall sequence of the template or nascent strand. Iterative processing and further data processing can be used to fill in any blanks, correct any erroneously called bases, or the like for a given sequence.

Figure 11:
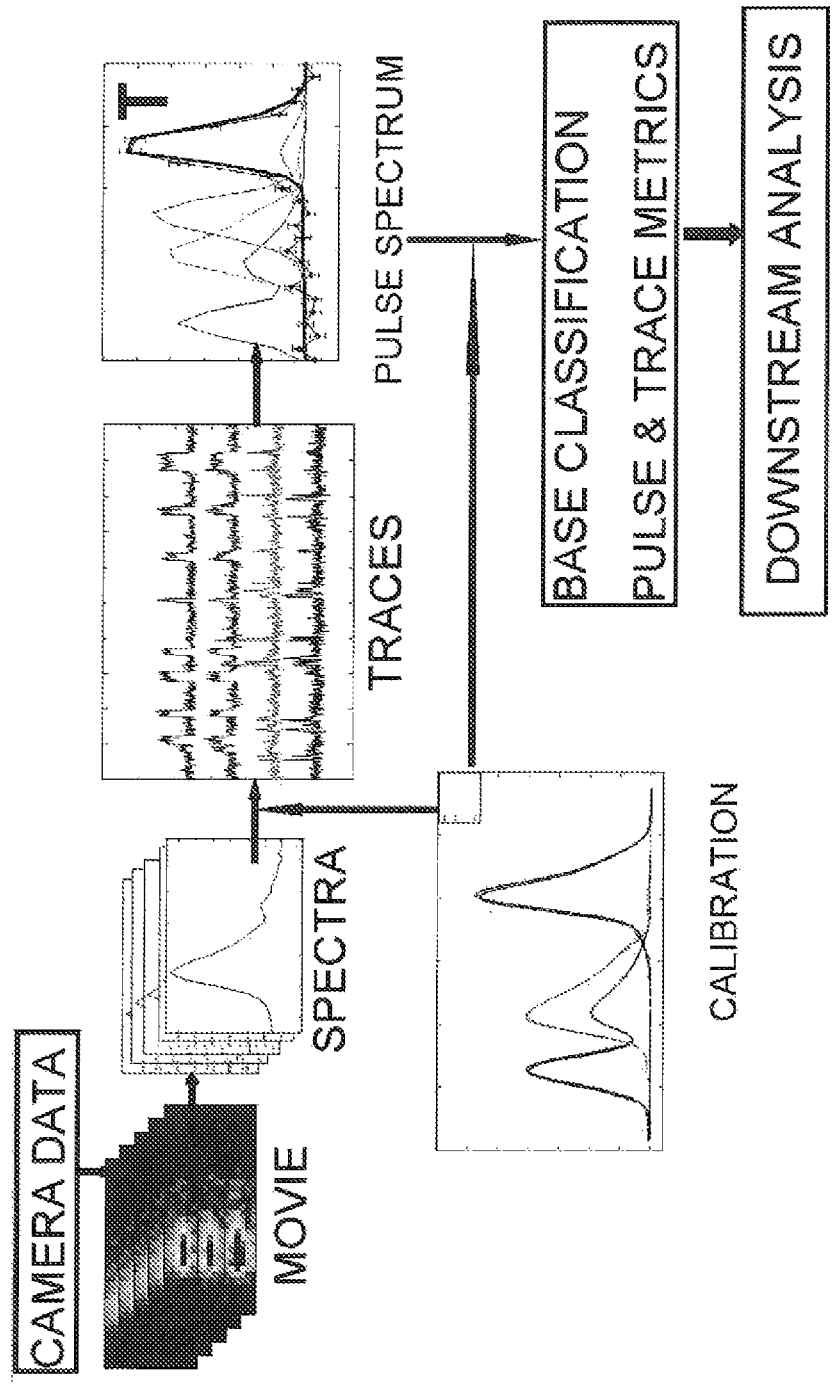
FIG. 11 shows a schematic illustrating a process of base calling and sequence determination.

Analysis of sequencing-by-incorporation-reactions on an array of reaction locations according to specific embodiments of the invention is also illustrated graphically in FIG. 11. In this summary figure, data captured by a camera is represented as a movie, which is also a time sequence of spectra. Spectral calibration templates are used to extract traces from the spectra. Pulses identifies in the traces are then used to return to the spectra data and from that data produce a temporally averaged pulse spectrum for each pulse, such pulse spectra will include spectra for events relating to enzyme conformational changes. The Spectral calibration templates are then also used to classify pulse spectrum to a particular base. Base classifications and pulse and trace metrics are then stored or passed to other logic for further analysis. The downstream analysis will include using the information from enzyme conformational changes to assist in the determination of incorporation events for base calling. Further base calling and sequence determination methods for use in the invention are described in copending U.S. patent application Ser. No. 12/134,186, filed Jun. 5, 2008.

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

What is claimed is:

1. A method of sequencing comprising;
providing a single polymerase enzyme complex comprising a polymerase enzyme, a nucleic acid template, and a primer; wherein the polymerase enzyme comprises a label which has a signal that changes when the enzyme undergoes a conformational change corresponding to translocation;
contacting the complex with sequencing reagents including two or more types of nucleotides or nucleotide analogs, each labeled with a different label, whereby enzyme mediated addition of nucleotides or nucleotide analogs to the primer to produce a growing strand complementary to the template occurs, wherein the labels on each of the two or more types of nucleotides or nucleotide analogs, and the label on the polymerase enzyme each provide a distinct signal;
monitoring in real time the distinct signals from the labels on each of the two or more types of nucleotides or nucleotide analogs, and the distinct signals from the label on the polymerase enzyme as the growing strand is produced;
determining the type of nucleotide or nucleotide analog that has been incorporated by observing signals from the labeled nucleotides or nucleotide analogs during the enzyme mediated addition;
determining whether a nucleotide or nucleotide analog is incorporated into the growing strand using observed signals from the labeled polymerase enzyme that are indicative of translocation; and
combining the determination of the type of nucleotide or nucleotide analog with the determination of whether a nucleotide or nucleotide analog is incorporated, whereby observing both a signal from the label on a type of nucleotide or nucleotide analog and a signal from the label on the polymerase enzyme corresponding to translocation within the same time period indicates that a nucleotide or nucleotide analog of that type has been incorporated in that time period, and whereby observing only a signal from the label on a type of nucleotide or nucleotide analog, and no signal from the label on the polymerase enzyme corresponding to translocation within the same time period indicates that no nucleotide or nucleotide analog has been incorporated in that time period, to obtain more accurate sequencing than without the determination of whether a nucleotide or nucleotide analog has been incorporated, whereby including the signals from the labeled polymerase reduces errors due to branching.

2. The method of claim 1 wherein the labels for the enzyme and the nucleotides or nucleotide analogs comprise fluorescent labels.

3. The method of claim 1 wherein the signal that changes when the enzyme undergoes a conformational change comprises a FRET signal from a donor and an acceptor.

4. The method of claim 3 wherein the donor and acceptor are both attached to the polymerase enzyme.

5. The method of claim 4 wherein the donor and acceptor are attached to portions of the enzyme which move relative to one another during a conformational change.

6. The method of claim 1 wherein the label whose signal changes when the enzyme undergoes a conformational change comprises a fluorescent label whose fluorescence is sensitive to changes in its local environment.

7. The method of claim 1 wherein the signal that changes when the enzyme undergoes a conformational change comprises quenching of a fluorescent label.

8. The method of claim 7 wherein the polymerase enzyme has both a fluorescent label and a quencher attached to different portions of the enzyme, and the quenching results from relative motions of the different portions of the enzyme from a conformational change.

9. The method of claim 1 wherein the polymerase enzyme comprises a DNA polymerase or an RNA polymerase.

10. The method of claim 9 wherein the template comprises DNA or RNA.

11. The method of claim 9 wherein the polymerase is a modified Type B polymerase.

12. The method of claim 1 wherein at least one label is attached to the fingers, palm, thumb, or exo domains.

13. A method for nucleic acid sequencing comprising:
providing a reaction mixture for nucleic acid polymerization comprising four types of nucleotides or nucleotide analogs, each having a different label;
contacting the reaction mixture with a polymerase enzyme complex comprising a polymerase enzyme, a template nucleic acid, and a primer; under conditions whereby enzyme mediated addition of nucleotides or nucleotide analogs to produce a growing nucleic acid strand from the primer occurs, wherein the enzyme comprises a label which exhibits a change in optical properties when the enzyme undergoes a conformational change corresponding to translocation, wherein the label on the enzyme provides a distinct signal to the labels on the four types of nucleotide or nucleotide analogs;
observing optical signals from the nucleotides or nucleotide analog and the enzyme while the nucleotides or nucleotide analogs are incorporated into the growing nucleic acid strand;

determining, using the observed optical signal from the nucleotides or nucleotide analogs, when a particular type of nucleotide or nucleotide analog is associated with the enzyme;

determining, using the observed optical signal from the label on the enzyme, when the enzyme undergoes a conformational change corresponding to translocation;

using the determination of when a particular nucleotide or nucleotide analog is associated with the enzyme to measure which type of nucleotide or nucleotide analog is incorporated in combination with the determination of when the enzyme undergoes conformational change corresponding to translocation to measure whether a nucleotide or nucleotide analog has been incorporated, to obtain a nucleic acid sequence of the template, whereby observing both a signal from the label on a type of nucleotide or nucleotide analog and a signal from the label on the polymerase enzyme corresponding to translocation within the same time period indicates that a nucleotide or nucleotide analog of that type has been incorporated in that time period, and whereby observing only a signal from the label on a type of nucleotide or nucleotide analog, and no signal from the label on the polymerase enzyme corresponding to translocation within the same time period indicates that no nucleotide or nucleotide analog has been incorporated in that time period, whereby including the determination of when the enzyme undergoes conformational change reduces errors due to branching.

14. The method of claim 13 wherein the labels for the enzyme and for the nucleotides or nucleotide analogs comprise fluorescent labels.

15. The method of claim 13 wherein the signal that changes when the enzyme undergoes a conformational change comprises a FRET signal from a donor and an acceptor.

16. The method of claim 15 wherein the donor and acceptor are both attached to the polymerase enzyme.

17. The method of claim 16 wherein the donor and acceptor are attached to portions of the enzyme which move relative to one another during a conformational change.

18. The method of claim 13 wherein the label whose signal changes when the enzyme undergoes a conformational change comprises a fluorescent label whose fluorescence is sensitive to changes in its local environment.

* * * * *